United States Patent
Lafleche et al.

(10) Patent No.: US 9,468,307 B2
(45) Date of Patent: Oct. 18, 2016

(54) INFLATABLE MATTRESS AND CONTROL METHODS

(71) Applicant: Stryker Corporation, Kalamazoo, MI (US)

(72) Inventors: Patrick Lafleche, Kalamazoo, MI (US);
Krishna Sandeep Bhimavarapu, Portage, MI (US); Manikantan Seshadrinathan, Portage, MI (US); Donna-Marie Robertson, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 601 days.

(21) Appl. No.: 13/836,813

(22) Filed: Mar. 15, 2013

(65) Prior Publication Data
US 2014/0059781 A1     Mar. 6, 2014

Related U.S. Application Data

(60) Provisional application No. 61/696,819, filed on Sep. 5, 2012.

(51) Int. Cl.
*A47C 27/08*     (2006.01)
*A61G 7/057*     (2006.01)

(52) U.S. Cl.
CPC ......... *A47C 27/083* (2013.01); *A61G 7/05769* (2013.01); *A61G 2203/34* (2013.01); *A61G 2203/40* (2013.01); *A61G 2203/42* (2013.01); *A61G 2203/44* (2013.01)

(58) Field of Classification Search
CPC  A47C 27/081; A47C 27/082; A47C 27/083; A47C 27/08; A47C 27/10; A61G 7/05769; A61G 7/05776; A61G 2203/34; A61G 2203/44

USPC ................. 5/713, 710, 706, 655.3, 654, 644
See application file for complete search history.

(56) References Cited

U.S. PATENT DOCUMENTS

| 4,127,906 A | 12/1978 | Zur |
| 4,713,854 A | 12/1987 | Graebe |

(Continued)

FOREIGN PATENT DOCUMENTS

| CA | 2606474 A1 | 10/2014 |
| FR | 2757377 A1 | 6/1998 |

(Continued)

OTHER PUBLICATIONS

International Written Opinion for PCT/US2013/057216, the international counterpart to U.S. Appl. No. 13/836,813.

(Continued)

*Primary Examiner* — Robert G Santos
(74) *Attorney, Agent, or Firm* — Warner Norcross & Judd LLP

(57) ABSTRACT

A patient support, such as a mattress, includes a plurality of inflatable bladders. Depth sensors are included in the support that measure the degree of penetration of a patient into the mattress. An air pressure sensor is also included that measures the pressure inside at least one bladder. A suitable inflation level of the mattress is determined by monitoring the rate of change of the depth with respect to air pressure as the bladder is either inflated or deflated. By detecting an inflection point in the graphical relationship of the depth and pressure outputs, a suitable inflation point for the bladders is determined that reduces interface pressures experienced by the patient, yet does not overly sink the patient into the mattress to a degree of discomfort. Analyzing the outputs of the depth and pressure sensors can also be used to detect a patient's heart rate and respiration rate.

25 Claims, 11 Drawing Sheets

(56) References Cited

U.S. PATENT DOCUMENTS

| | | | |
|---|---|---|---|
| 4,730,610 A | 3/1988 | Graebe | |
| 4,833,457 A | 5/1989 | Graebe, Jr. | |
| 4,864,671 A | 9/1989 | Evans | |
| 4,873,737 A | 10/1989 | Savenije | |
| 4,953,247 A * | 9/1990 | Hasty | A61G 7/05776 |
| | | | 137/625.66 |
| 4,962,552 A | 10/1990 | Hasty | |
| 4,989,283 A | 2/1991 | Krouskop | |
| 5,052,068 A | 10/1991 | Graebe | |
| 5,088,136 A | 2/1992 | Stryker et al. | |
| 5,111,544 A | 5/1992 | Graebe | |
| 5,152,023 A | 10/1992 | Graebe | |
| 5,163,196 A | 11/1992 | Graebe et al. | |
| 5,179,742 A | 1/1993 | Oberle | |
| 5,235,713 A | 8/1993 | Guthrie et al. | |
| 5,317,773 A | 6/1994 | Graebe | |
| 5,325,551 A | 7/1994 | Tappel et al. | |
| 5,364,162 A | 11/1994 | Bar et al. | |
| 5,369,828 A | 12/1994 | Graebe | |
| 5,410,297 A | 4/1995 | Joseph et al. | |
| 5,461,741 A | 10/1995 | Graebe | |
| 5,502,855 A | 4/1996 | Graebe | |
| 5,539,942 A | 7/1996 | Melou | |
| 5,542,136 A | 8/1996 | Tappel | |
| 5,551,107 A | 9/1996 | Graebe | |
| 5,560,374 A | 10/1996 | Viard | |
| 5,561,875 A | 10/1996 | Graebe | |
| 5,596,781 A | 1/1997 | Graebe | |
| 5,613,257 A | 3/1997 | Graebe | |
| 5,640,728 A | 6/1997 | Graebe | |
| 5,689,845 A | 11/1997 | Sobieralski | |
| 5,808,552 A | 9/1998 | Wiley et al. | |
| 5,815,864 A | 10/1998 | Sloop | |
| 5,845,352 A | 12/1998 | Matsler et al. | |
| 5,913,774 A | 6/1999 | Feddema | |
| 5,934,280 A * | 8/1999 | Viard | A61G 7/05769 |
| | | | 128/845 |
| 5,944,066 A | 8/1999 | Viard | |
| 5,947,168 A | 9/1999 | Viard | |
| 6,009,580 A | 1/2000 | Caminade et al. | |
| 6,018,832 A | 2/2000 | Graebe | |
| 6,034,526 A | 3/2000 | Montant et al. | |
| 6,067,019 A | 5/2000 | Scott | |
| 6,079,068 A | 6/2000 | Viard | |
| 6,094,762 A | 8/2000 | Viard et al. | |
| 6,095,611 A | 8/2000 | Bar et al. | |
| 6,154,907 A | 12/2000 | Cinquin | |
| 6,165,142 A | 12/2000 | Bar | |
| 6,244,272 B1 | 6/2001 | Montant et al. | |
| 6,289,537 B1 | 9/2001 | Hopper et al. | |
| 6,297,738 B1 | 10/2001 | Newham | |
| 6,351,863 B1 | 3/2002 | Meyer et al. | |
| 6,385,803 B1 | 5/2002 | Viard | |
| 6,425,153 B1 | 7/2002 | Reswick | |
| 6,487,739 B1 | 12/2002 | Harker | |
| 6,560,804 B2 | 5/2003 | Wise et al. | |
| 6,564,410 B2 | 5/2003 | Graebe et al. | |
| 6,623,080 B2 | 9/2003 | Clapper | |
| 6,687,936 B2 | 2/2004 | Graebe et al. | |
| 6,687,937 B2 | 2/2004 | Harker | |
| 6,789,284 B2 | 9/2004 | Kemp | |
| 6,807,695 B1 | 10/2004 | Barr | |
| 6,825,765 B2 | 11/2004 | Stanley et al. | |
| 6,855,158 B2 | 2/2005 | Stolpmann | |
| 6,901,617 B2 | 6/2005 | Sprouse, II et al. | |
| 7,098,674 B2 | 8/2006 | Stanley et al. | |
| 7,414,536 B2 | 8/2008 | Call et al. | |
| 7,424,761 B1 | 9/2008 | Graebe | |
| 7,469,436 B2 | 12/2008 | Meyer et al. | |
| 7,583,199 B2 | 9/2009 | Graebe, Jr. | |
| 7,681,264 B2 | 3/2010 | Graebe | |
| 7,698,765 B2 | 4/2010 | Bobey et al. | |
| 7,752,926 B2 * | 7/2010 | Caminade | A61B 5/447 |
| | | | 73/862.625 |
| 7,802,332 B2 | 9/2010 | Kummer et al. | |
| 7,845,032 B2 | 12/2010 | Chambers et al. | |
| 7,849,544 B2 | 12/2010 | Flocard et al. | |
| 8,006,333 B2 | 8/2011 | Genaro et al. | |
| 8,011,043 B2 | 9/2011 | Graebe et al. | |
| 8,031,080 B2 | 10/2011 | Price et al. | |
| 8,038,632 B2 | 10/2011 | Flick et al. | |
| 8,048,005 B2 | 11/2011 | Dixon et al. | |
| 8,056,163 B2 | 11/2011 | Lemire et al. | |
| 8,056,165 B2 | 11/2011 | Kummer et al. | |
| 8,090,478 B2 | 1/2012 | Skinner et al. | |
| 8,102,270 B2 | 1/2012 | Gowda et al. | |
| 8,104,125 B2 | 1/2012 | Soltani et al. | |
| 8,104,126 B2 * | 1/2012 | Caminade | A61G 7/05776 |
| | | | 5/655.3 |
| 8,347,436 B2 | 1/2013 | Flick et al. | |
| 8,413,271 B2 | 4/2013 | Blanchard et al. | |
| 8,595,873 B2 * | 12/2013 | Hornbach | A61G 7/015 |
| | | | 5/710 |
| 8,598,893 B2 * | 12/2013 | Camus | G01L 1/142 |
| | | | 324/658 |
| 8,620,477 B2 * | 12/2013 | Skinner | A61G 7/05769 |
| | | | 700/281 |
| 8,698,509 B2 | 4/2014 | Call et al. | |
| 8,745,788 B2 * | 6/2014 | Bhai | A61G 7/05769 |
| | | | 5/600 |
| 8,997,588 B2 | 4/2015 | Taylor | |
| 9,038,221 B2 * | 5/2015 | Fraser | A61G 5/1043 |
| | | | 5/654 |
| 2002/0066143 A1 | 6/2002 | Graebe et al. | |
| 2003/0030319 A1 | 2/2003 | Clapper | |
| 2005/0200489 A1 * | 9/2005 | Sloop | A61B 5/1036 |
| | | | 340/573.7 |
| 2006/0064820 A1 * | 3/2006 | Call | A61G 5/1043 |
| | | | 5/654 |
| 2006/0244466 A1 | 11/2006 | Call et al. | |
| 2008/0189865 A1 | 8/2008 | Bhai | |
| 2008/0307582 A1 * | 12/2008 | Flocard | A61G 7/05769 |
| | | | 5/712 |
| 2009/0000037 A1 * | 1/2009 | Graebe, Jr. | A47C 27/083 |
| | | | 5/654 |
| 2009/0056020 A1 * | 3/2009 | Caminade | A61B 5/447 |
| | | | 5/600 |
| 2009/0100604 A1 * | 4/2009 | Caminade | A61G 7/05776 |
| | | | 5/713 |
| 2009/0144909 A1 | 6/2009 | Skinner et al. | |
| 2009/0217457 A1 | 9/2009 | Graebe et al. | |
| 2010/0063638 A1 * | 3/2010 | Skinner | A61G 7/05769 |
| | | | 700/281 |
| 2010/0132116 A1 | 6/2010 | Stacy et al. | |
| 2010/0194159 A1 | 8/2010 | Goeckel | |
| 2010/0205750 A1 | 8/2010 | McCausland et al. | |
| 2010/0308846 A1 * | 12/2010 | Camus | G01L 1/142 |
| | | | 324/679 |
| 2011/0068939 A1 | 3/2011 | Lachenbruch | |
| 2011/0092890 A1 | 4/2011 | Stryker et al. | |
| 2011/0144548 A1 | 6/2011 | Elliott et al. | |
| 2011/0209287 A1 | 9/2011 | Call et al. | |
| 2011/0289691 A1 | 12/2011 | Lafleche et al. | |
| 2011/0296623 A1 | 12/2011 | Lafleche et al. | |
| 2011/0301516 A1 | 12/2011 | Lafleche et al. | |
| 2012/0004789 A1 | 1/2012 | Wilker, Jr. | |
| 2012/0013452 A1 | 1/2012 | McNeely et al. | |
| 2012/0036646 A1 | 2/2012 | McCausland et al. | |
| 2012/0054965 A1 | 3/2012 | Kummer et al. | |
| 2012/0144595 A1 * | 6/2012 | Hornbach | A61G 7/015 |
| | | | 5/713 |
| 2012/0174322 A1 * | 7/2012 | Skinner | A61G 7/05769 |
| | | | 5/713 |
| 2013/0061396 A1 | 3/2013 | Lafleche et al. | |
| 2013/0091961 A1 | 4/2013 | Taylor | |
| 2014/0059781 A1 * | 3/2014 | Lafleche | A47C 27/083 |
| | | | 5/713 |
| 2014/0082849 A1 * | 3/2014 | Hornbach | A61G 7/015 |
| | | | 5/713 |

(56) References Cited

U.S. PATENT DOCUMENTS

| | | |
|---|---|---|
| 2014/0090488 A1 | 4/2014 | Taylor et al. |
| 2014/0230153 A1* | 8/2014 | Fraser .................. A61G 5/1043 5/654 |

FOREIGN PATENT DOCUMENTS

| | | |
|---|---|---|
| WO | 9736521 | 10/1997 |
| WO | 2011006093 A1 | 1/2011 |
| WO | 2011097569 A2 | 8/2011 |
| WO | 2015121822 A1 | 8/2015 |

OTHER PUBLICATIONS

European Search Report dated Mar. 24, 2016, for European patent application EP 13834564, corresponding to U.S. Appl. No. 13/836,813.

European Written Opinion dated Mar. 24, 2016, for European patent application EP 13834564, corresponding to U.S. Appl. No. 13/836,813.

* cited by examiner

INFLATABLE MATTRESS AND CONTROL METHODS

This application claims priority to U.S. provisional patent application Ser. No. 61/696,819 filed Sep. 5, 2012 by applicants Patrick Lafleche et al. and entitled INFLATABLE MATTRESS AND CONTROL METHODS, the complete disclosure of which is hereby incorporated herein by reference.

BACKGROUND OF THE INVENTION

The present invention relates to mattresses used for supporting individuals thereon, and more particularly to mattresses that are used in healthcare settings and that have one or more inflatable zones.

In health care settings, mattresses are used to support patients positioned on beds, stretchers, cots, and the like. In many instances, such mattresses include one or more inflatable bladders whose inflation levels can be controlled. In order to reduce the likelihood of the patient developing bed sores, or aggravating pre-existing bed sores, the inflation level of the bladders should be set to so as to distribute the patient's weight over as great an area as possible, or over an area large enough to reduce undesired force concentrations on the patient's body. By supporting the patient's weight over a greater surface area on the mattress, the interface pressure between the patient and the mattress is reduced. However, if the patient is allowed to sink too deeply into the mattress, the patient may experience feelings of discomfort. Further, it can be difficult for a caregiver to manually determine a proper inflation level that sufficiently distributes the patient's weight and that balances the patient's desire for comfort.

SUMMARY OF THE INVENTION

The various aspects of the present invention provide patient supports, such as mattresses, that have inflation levels that may be automatically determined by one or more controllers, thereby avoiding the need for caregivers to manually determine inflation levels. Further, the one or more controllers determine inflation levels that are suitable for both distributing patient pressure, and thereby reducing bed sore sores, and for creating a comfortable support surface for the patient. In some aspects, the mattress automatically determines a suitable inflation level for each individual patient that positions himself or herself on the mattress, thereby creating an individualized inflation level that is tailored to that specific individual. In other aspects, the mattress re-determines the suitable inflation level based on one or more triggering events, such as, but not limited to, a patient re-entering the mattress, another individual positioning themselves on the mattress, an angular change of the entire mattress or of one section of the mattress with respect to another, an object being positioned on the mattress, or a person manually instructing the mattress to re-determine the suitable inflation level. Still further, in some embodiments, the controller determines the suitable inflation level by monitoring the rate of change of the patient immersion depth with respect to the rate of change of air pressure inside of the one or more bladders.

According to a first embodiment, a patient support is provided that includes an inflatable bladder, a depth sensor, an air pressure sensor, and a controller. The depth sensor generates a depth signal indicative of how deeply a patient positioned on the patient support sinks into the inflatable bladder, and the air pressure sensor generates an air pressure signal indicative of a level of air pressure inside of the inflatable bladder. The controller determines a suitable inflation level of the bladder by monitoring a rate of change of the depth signal with respect to the air pressure signal as the air pressure inside the bladder is changed.

According to a second embodiment, a patient support is provided that includes an inflatable bladder, a first depth sensor, a second depth sensor, an air pressure sensor, and a controller. The first depth sensor generates a first depth signal indicative of how deeply a patient positioned on the patient support sinks into a first portion of the inflatable bladder, and the second depth sensor generates a second depth signal indicative of how deeply a patient positioned on said patient support sinks into a second portion of the inflatable bladder. The air pressure sensor generates an air pressure signal indicative of a level of air pressure inside of the inflatable bladder. The controller determines a suitable inflation level of the bladder by monitoring a rate of change of the first depth signal with respect to the air pressure signal and by monitoring a rate of change of the second depth signal with respect to the air pressure signal.

According to a third embodiment, a patient support is provided that includes a first section having a first inflatable bladder, a second section having a second inflatable bladder, a depth sensor, an air pressure sensor, and a controller. The second section is positioned in an area adapted to support a sacral region of a patient when the patient lies on the patient support. The depth sensor generates depth signals indicative of how deeply a patient positioned on the patient support sinks into the second inflatable bladder. The air pressure sensor generates air pressure signals indicative of a level of air pressure inside of the second inflatable bladder; and the controller determines a suitable inflation level of the second bladder based upon the depth signals and the air pressure signals. The controller also determines a suitable inflation level of the first bladder based upon the suitable inflation level of the second bladder.

According to a fourth embodiment, a patient support is provided that includes an inflatable bladder, a depth sensor, an air pressure sensor, and a controller. The depth sensor generates a depth signal indicative of how deeply a patient positioned on the patient support sinks into the inflatable bladder. The air pressure sensor generates an air pressure signal indicative of a level of air pressure inside of the inflatable bladder. The controller determines a suitable inflation level of the bladder after a patient is positioned on the patient support. The controller also automatically re-determines the suitable inflation level after at least one triggering event selected from the following: (1) the patient exits the patient support and subsequently returns to the patient support; (2) another person sits on the patient support; (3) an object is placed on the patient support; (4) an angular orientation at least a portion the patient support is changed; and (5) the patient moves on the patient support more than a threshold amount.

According to a fifth embodiment, a method of controlling an inflation level of a plurality of inflatable bladders in a mattress is provided. The method includes measuring how far a patient sinks into a first inflatable bladder; measuring how far a patient sinks into a second inflatable bladder that is hermetically isolated from the first inflatable bladder; and setting the air pressure inside both the first and second inflatable bladders to a common inflation level that is determined based upon the depth measurement from at least one of the first and second inflatable bladders.

According to a sixth embodiment, a patient support is provided that includes a cover, first and second sections, a depth sensor, an air pressure sensor, an angle sensor, and a controller. The first section includes a first inflatable bladder positioned inside of the cover in a region of the mattress adapted to support a patient's back. The second section includes a second inflatable bladder positioned inside of the cover in a region of the mattress adapted to support a patient's sacral region. The depth sensor generates depth signals indicative of how deeply a patient positioned on said patient support sinks into the second inflatable bladder. The air pressure sensor generates air pressure signals indicative of a level of air pressure inside of the second inflatable bladder. The angle sensor generates angular measurement signals indicative of an angular orientation of the first section with respect to the second section, and the controller determines a suitable inflation level of the second bladder based upon the depth signals and the air pressure signals. The controller also automatically re-determines the suitable inflation level if the angular signals change by more than a threshold amount.

According to a seventh embodiment, a patient support is provided that includes an inflatable bladder, first and second depth sensors, and a controller. The first depth sensor generates first depth signals indicative of how deeply a patient positioned on the patient support sinks into a first portion of the patient support. The second depth sensor generates second depth signals indicative of how deeply a patient positioned on the patient support sinks into a second portion of the patient support; and the controller monitors the first and second depth signals to determine when a patient positioned on the patient support has moved more than a threshold amount. The controller also automatically adjusts an inflation level inside of the inflatable bladder after the controller detects that the patient has moved more than the threshold amount.

According to still other embodiments, any of the aforementioned seven embodiments may be further modified to include any one or more of the following features, steps, or characteristics, to the extent such embodiments do not already include the following. The controller may adapted determine the suitable inflation level after detecting an inflection point in a plot of the depth signals versus the air pressure signals. The controller may monitors the rate of change of the depth signals with respect to the air pressure signals as the air pressure is lowered inside the bladder. Alternatively, the controller may monitor the rate of change of the depth signals with respect to the air pressure signals as the air pressure is raised inside the bladder.

The controller may set the suitable inflation level equal to an air pressure at which a derivative of the depth signal with respect to the air pressure signal is substantially equal to a local minimum. The inflatable bladder may be incorporated into a mattress and positioned at a location adapted to support a patient's sacral area.

The inflatable bladder or bladders may all include pods.

The suitable inflation level may be determined without consulting any stored data previously gathered from multiple individuals of varying weight and/or varying body morphology.

The depth sensor or depth sensors may be capacitive sensors. In some embodiments, the capacitive depth sensors include a capacitive plate positioned generally horizontally underneath the inflatable bladder, and a flexible, electrically conductive sheet positioned above the inflatable bladder.

The patient support may be incorporated into a bed frame having a support surface thereon on which the patient support is supported. The bed frame may include a control panel adapted to control inflation of the bladder. The control panel may further include a control for causing the controller to re-determine the suitable inflation level when manipulated by a user.

The controller may re-determine the suitable inflation level by inflating the bladder to a desired pressure, allowing air to escape from the bladder, and monitoring the rate of change of the depth signals with respect to the air pressure signals as the air pressure inside the bladder is decreased.

In some embodiment, one or more additional inflatable bladders may be included that do not include any depth sensors. Such additional inflatable bladders may have their inflation levels set at one or more fixed ratios with respect to the suitable inflation level determined by the controller. Alternatively, such additional inflatable bladders may have their inflation levels set at a fixed offset with respect to the suitable inflation levels determined by the controller. Still further, in yet other embodiments, some of the additional bladders may have their air pressure set at a fixed ratio with respect to the suitable inflation level, while others of the additional bladders may have their air pressure set at a fixed offset from the suitable inflation level.

The patient support may automatically re-determine the suitable inflation level when any one or more of the following triggering events occur: movement of the patient on the patient support exceeds a threshold, angular changes are made to at least a portion of the mattress, a patient moves onto the patient support, an additional person moves onto the patient support, or an object is placed on the patient support.

One or more turning bladders may be included in the patient support apparatus that are hermetically isolated from the other inflatable bladders and that are adapted to help turn a patient positioned on the patient support when inflated. Such turn bladders may be positioned underneath the inflatable bladder(s) having the depth sensor(s).

Third, fourth, and even more than four depth sensors may be used to provide depth signals indicative of how deeply a patient positioned on the patient support sinks into various portions of one or more bladders. The controller can monitor the multiple depth sensors to determine patient movement and/or to determine a suitable inflation level for one or more bladders in the patient support.

The suitable inflation level may be determined by controlling a release of air from, or an addition of air to, the inflatable bladder while monitoring the rates of change of the depth signals and the air pressure signals.

According to yet another embodiment, a patient support is provided that includes an inflatable bladder, a depth sensor, an air pressure sensor, and a controller. The depth sensor generates a depth signal indicative of how deeply a patient positioned on the patient support sinks into the inflatable bladder, and the air pressure sensor generates an air pressure signal indicative of a level of air pressure inside of the inflatable bladder. The controller monitors both changes in the depth and changes in the pressure and uses these changes to determine a patient's heart rate and/or respiration rate while positioned on the patient support.

According to other aspects, the determination of heart and/or respiration rate are performed non-invasively without having to connect any sensor to the patient. The monitoring of these vital signs is performed automatically while the patient is positioned on the patient support. These vital signs are made available for transmission via a wired or wireless connection to a remote location. These vital signs are also made available for transmitting to the bed, stretcher, or cot on which the patient support is positioned.

Before the embodiments of the invention are explained in more detail below, it is to be understood that the invention is not limited to the details of operation or to the details of construction and the arrangement of the components set forth in the following description or illustrated in the drawings. The invention may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE EMBODIMENTS

Figure 1:
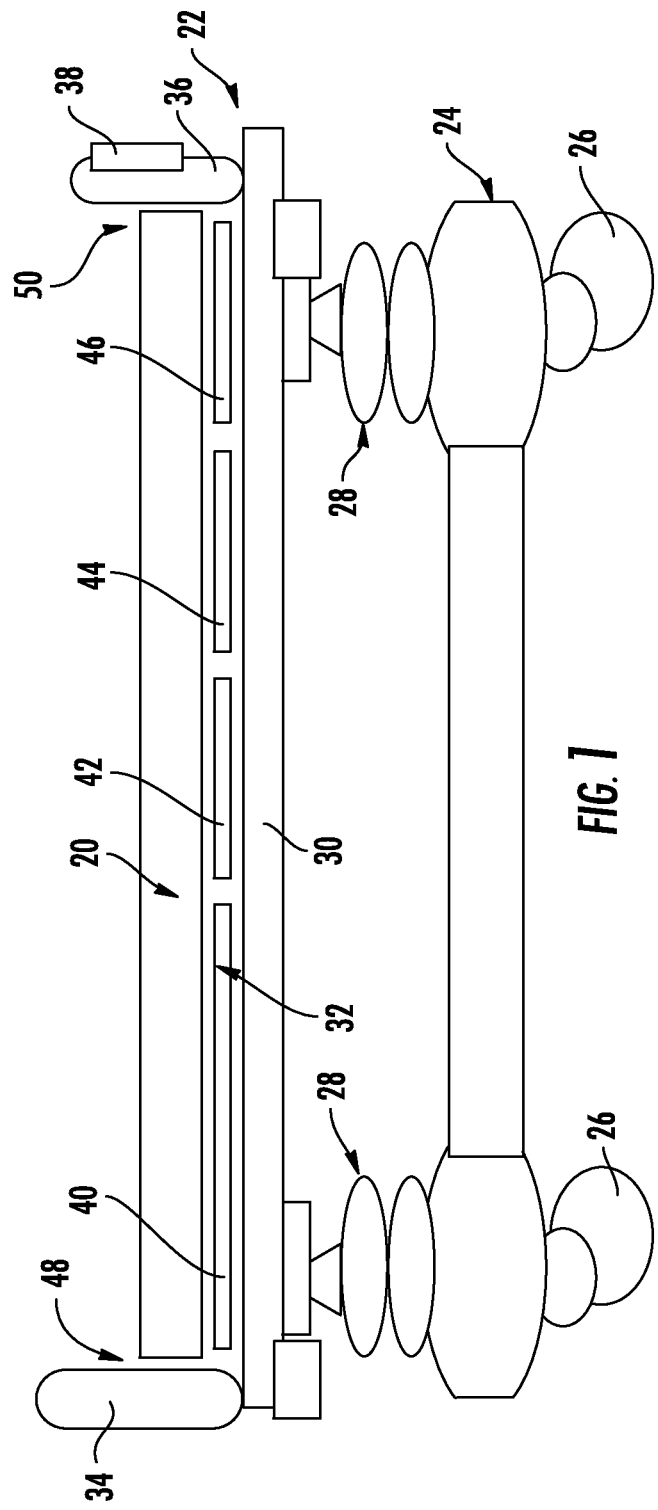
FIG. 1 is a side elevation diagram of a patient support apparatus into which a patient support of the present invention may be integrated.

FIG. 1 illustrates a patient support 20 according to one embodiment of the invention. In the example of FIG. 1, patient support 20 is a mattress. However, it will be understood that patient support 20 may take on other manifestations, such as cushions, pads, etc. Indeed, in one embodiment, patient support 20 may be a cushion or pad for a chair, such as a wheelchair or a stationary chair. In general, patient support 20 finds applicability wherever and whenever a patient is to be supported on a surface and it is desirable to reduce interface pressures experienced by the patient while positioned on the patient support.

In the embodiment shown in FIG. 1, patient support 20 is supported on a patient support apparatus 22 that, in this particular embodiment, is a bed. Patient support apparatus 22 may take on other forms besides beds, such as, but not limited to, cots, stretchers, operating tables, gurneys, and the like. Patient support apparatus 22 may be a conventional support apparatus that is commercially available and that merely provides a supporting function for patient support 20. In other embodiments, patient support apparatus 22 includes one or more controls that are integrated therein and which are used in controlling the operation of patient support 20, as will be discussed in greater detail below.

As shown in FIG. 1, patient support apparatus 22 includes a base 24 having a plurality of wheels 26, a pair of elevation adjustment mechanisms 28 supported on base 24, a frame or litter 30 supported on elevation adjustment mechanisms 28, and a patient support deck 32 supported on frame 30. Patient support apparatus 22 also includes a headboard 34 and a footboard 36. Either or both of headboard 34 and footboard 36 may be removable from frame 30 and may include one or more electrical connectors for establishing electrical communication between electronic components on or in footboard 36 and/or headboard 34 and other electronic components supported on or in frame 30. Such electrical connector(s) may include any one or more of the connectors disclosed in commonly assigned U.S. patent application Ser. No. 13/790,762, filed Mar. 8, 2013, by applicants Krishna Bhimavarapu and entitled PATIENT SUPPORT APPARATUS CONNECTORS, the complete disclosure of which is incorporated herein by reference. Other types of connectors may also be used.

In one embodiment, electrical connectors are provided for establishing an electrical link between a user interface 38 that is positioned on, or integrated into, footboard 36 and patient support 20. User interface may take on a variety of different forms, such as, but not limited to, a touch screen, a Liquid Crystal Display (LCD), a plurality of buttons, switches, knobs, or the like, or any combination of these components. As will be described in more detail below, user interface 38 allows a user to control the operation of patient support 20. The electrical connection between user interface 38 and patient support 20 may take on different forms, including a direct electrical cable that runs from footboard 36 to patient support 20. In another embodiment, footboard 36 include electrical connectors that electrically couple user interface 38 to circuitry supported on frame 30. This circuitry is further in electrical communication with a port (not shown) to which an electrical cable from patient support 20 may be inserted, thereby establishing an electrical link between user interface 38 and patient support 20. In still other embodiments, communication between user interface 38 and patient support 20 is entirely wireless. An example of such wireless communication is disclosed in commonly assigned, U.S. patent application Ser. No. 13/802,992, filed Mar. 24, 2013, by applicants Michael Hayes et al. and entitled COMMUNICATION SYSTEMS FOR PATIENT SUPPORT APPARATUSES, the complete disclosure of which is hereby incorporated herein by reference.

Elevation adjustment mechanisms 28 are adapted to raise and lower frame 30 with respect to base 24. Elevation adjustment mechanisms 28 may be implemented as hydraulic actuators, electric actuators, or any other suitable device for raising and lowering frame 30 with respect to base 24. In the illustrated embodiment of FIG. 1, elevation adjustment mechanisms 28 are operable independently so that the orientation of frame 30 with respect to base 24 may also be adjusted. This allows support apparatus 22 to tilt a patient supported on patient support 20 to either the Trendelenburg orientation, or the reverse Trendelenburg orientation.

Frame 30 provides a structure for supporting patient support deck 32, headboard 34, and footboard 36. Patient support deck 32 provides a surface on which patient support 20 is positioned so that a patient may lie and/or sit thereon. Patient support deck 32 is made of a plurality of sections, some of which may be pivotable about generally horizontal pivot axes. In the embodiment shown in FIG. 1, patient support deck 32 includes a head or back section 40, a seat section 42, a thigh section 44, and a foot section 46. In other embodiments, patient support deck 32 may include fewer or greater numbers of sections. Head section 40, which is also sometimes referred to as a Fowler section, is pivotable between a generally horizontal orientation (shown in FIG. 1) and a plurality of raised positions (not shown in FIG. 1). Thigh section 44 and foot section 46 may also be pivotable about horizontal pivot axes.

The general construction of any of base 24, elevation adjustment mechanisms 28, frame 30, patient support deck 32, headboard 34, and/or footboard 36 may take on any known or conventional design, such as, for example, that disclosed in commonly assigned, U.S. Pat. No. 7,690,059 issued to Lemire et al., and entitled HOSPITAL BED, the complete disclosure of which is incorporated herein by reference; or that disclosed in commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is also hereby incorporated herein by reference. The construction of any of base 24, elevation adjustment mechanisms 28, frame 30, patient support deck 32, headboard 34, and/or footboard 36 may also take on forms different from what is disclosed in the aforementioned patent and patent publication.

In some embodiments, the operation of patient support 20 is based at least partially upon sensor data that originates from sensors integrated into patient support apparatus 22, while in other embodiments, patient support 20 operates solely on sensor data originating from sensors positioned internally inside of support 20. For those embodiments in which patient support 20 uses sensor data from patient support apparatus 22, such sensor data includes angle data and/or weight data. More specifically, patient support apparatus 22, in some embodiments, includes one or more angle sensors that detect the angular orientation (with respect to horizontal) of frame 30, as well as one or more angle sensors that detect the angular orientation (with respect to horizontal) of one or more of the sections of support deck 32. Still further, patient support apparatus 22, in some embodiments, includes a load cell system that detects patient weight and/or a center of gravity of a patient positioned on patient support 20. One such load cell system that may be used in patient support apparatus 22 is disclosed in commonly assigned U.S. Pat. No. 5,276,432 issued to Travis, the complete disclosure of which is incorporated herein by reference.

Other load cell systems may also be used. Regardless of the specific load cell system used, patient support apparatus 22 may communicate any one or more of patient weight, patient center of gravity, the angular orientation of frame 30, and/or the angular orientation of one or more of deck sections 40-46 to patient support 20, which may use this data in manners that will be discussed in more detail below.

Figure 2:
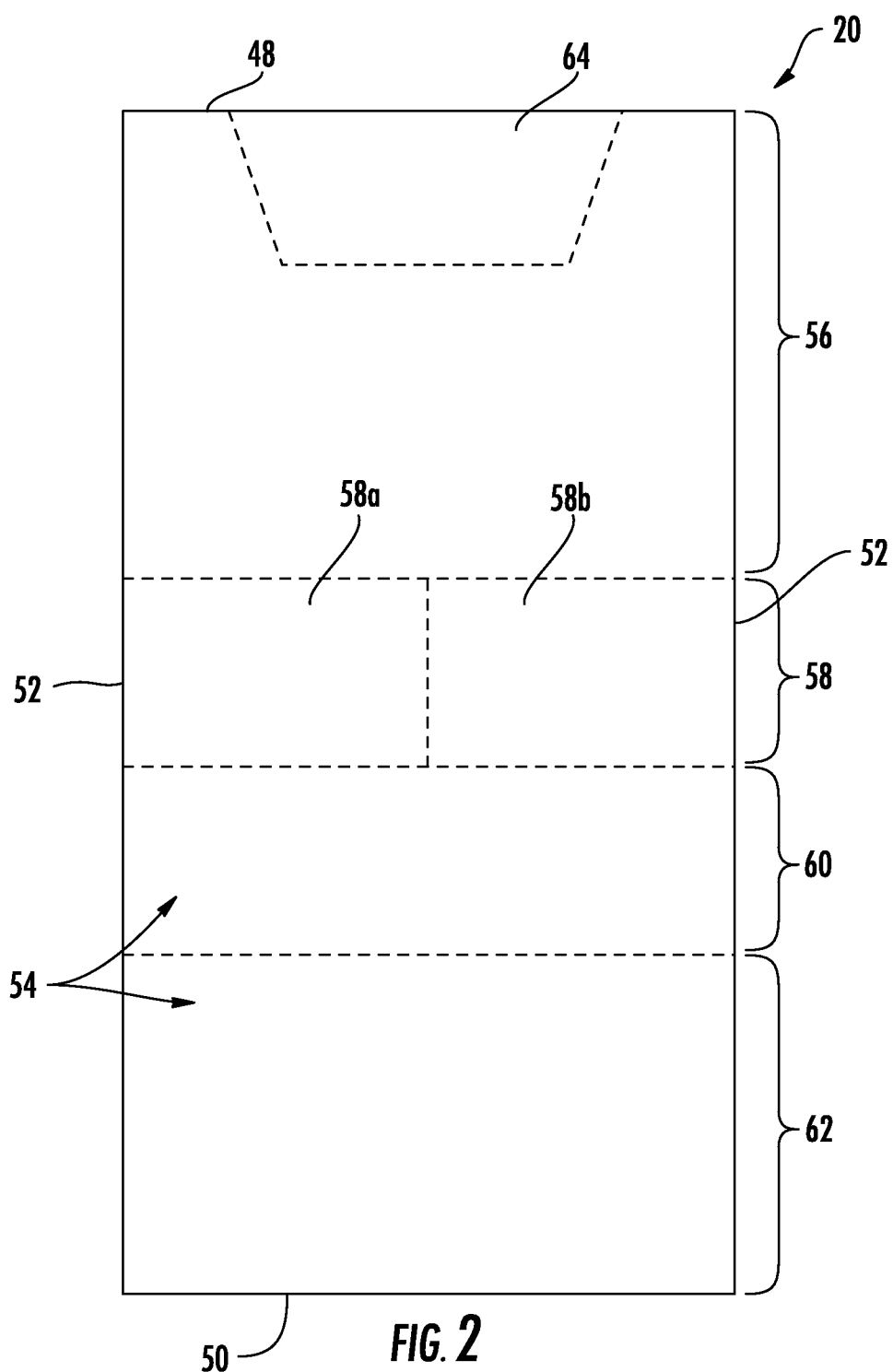
FIG. 2 is a plan view diagram of an embodiment of a patient support according to the present invention.

As shown in FIG. 2, patient support 20 includes a head end 48, a foot end 50, and a pair of sides 52. In the embodiment shown in FIG. 2, head end 48 of patient support 20 is intended to support a patients' head while foot end 50 is intended to support the patient's feet. Patient support 20 is further divided into a number of zones 54 that are illustrated in dashed lines in FIG. 2. Zones 54 represent areas of patient support 20 that can be controlled, in at least one aspect, differently from each other, and/or that are constructed differently from each other. For example, and as will be discussed in greater detail below, patient support 20 includes a right seat zone 58a and a left seat zone 58b. Each seat zone 58a and 58b includes a corresponding bladder, and the inflation of the bladder in right seat zone 58a can be controlled independently of the inflation of the bladder in left seat zone 58b.

As is also shown in FIG. 2, patient support 20 further includes a back zone 56, a thigh zone 60, and a foot zone 62. Back zone 56, in the illustrated embodiment, includes a head zone or pillow zone 64. The physical boundaries of each of the zones may be modified from that shown, as well as the number of locations of each zone. In the embodiment of FIG. 2, back zone 56 is positioned such that it will generally be aligned with head or back section 40 of patient support apparatus 22 when patient support 20 is positioned on support deck 32. Similarly, seat zone 58 will be generally aligned with seat section 42, thigh zone 60 will be generally aligned with thigh section 44, and foot zone 62 will be generally aligned with foot section 46. Such alignment, however, is not necessary. Indeed, patient support 20 may be used on support apparatuses 22 in which the support deck 32 has no individual sections, or which has a fewer or greater number than the four shown in FIG. 1.

As was noted above, seat zone 58, in the embodiment shown in FIG. 2, is subdivided into right and left sides. That is, seat zone 58 includes a right seat zone 58a and a left seat zone 58b. Each of seat zones 58a and 58b define regions in which hermetically isolated bladders are positioned so that the inflation level corresponding to right seat zone 58a can be controlled and/or set independently of the inflation level corresponding to left seat zone 58b. In this manner, if a patient is lying on his or her side, or is otherwise positioned closer to one side 52 than the other, zones 58a and 58b can be set, at least in some embodiments, to different inflation levels. Alternatively, it may be desirable to set the inflation levels for zones 58a and 58b differently in situations where the patient is positioned more toward the middle of patient support 20. In alternative embodiments, seat zone 58 could be a single zone that does not have separate subdivisions between the right and left side, but rather was inflatable and deflatable in a unitary manner. In still other alternative embodiments, one or more of the other zones 56, 60, and/or 62 could be subdivided into left and right sub-zones, or sub-divided in still other manners.

Figure 3:
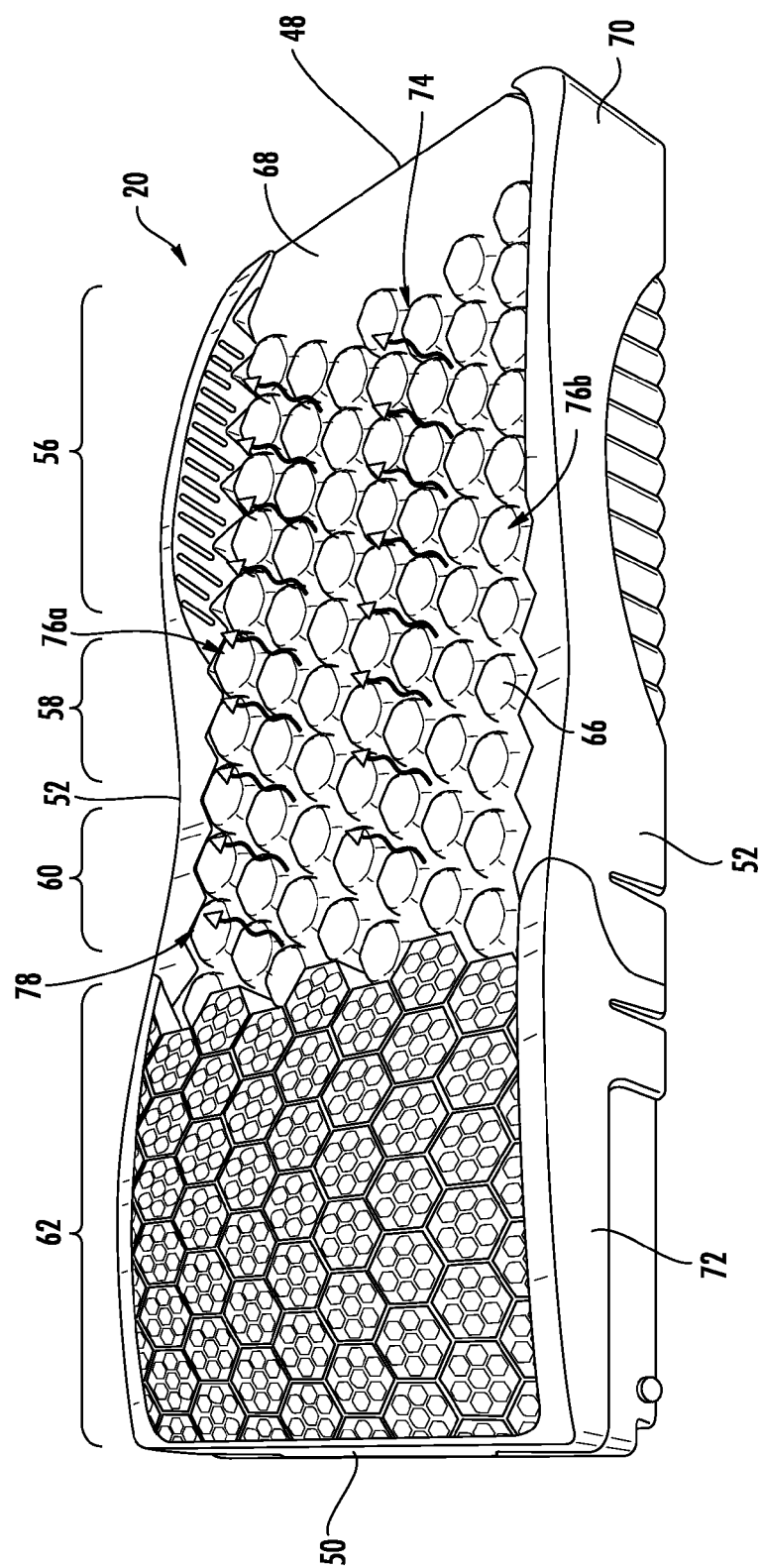
FIG. 3 is a perspective view of the patient support of FIG. 2 shown with a cover removed.

FIG. 3 illustrates patient support 20 with its outer cover removed, exposing a plurality of inflatable pods 66, as well as a pillow bladder 68, a foam crib 70 that supports pods 66, and a plurality of molded foot end cushioning 72. Foam cushioning 72 is not inflatable, but instead provides cushioned support to a patient's feet through its soft pliability.

Inflatable pods 66 are fluidly coupled together in a manner that corresponds to zones 54. That is, all of the pods 66 within back zone 56 inflate and deflate together, and can be inflated and deflated separately from the pods 66 in any of the other zones. Similarly, all of the pods in right seat zone 58a, all of the pods in left seat zone 58b, as well as all of the pods in thigh zone 60, are respectively able to be inflated and deflated together, as well as separately from the pods 66 in the other zones. Thus, the pods 66 in back zone 56 collectively define a back bladder 74, the pods 66 in right seat zone 58a collectively define a right seat bladder 76a, the pods 66 in left seat zone 58b collectively define a left seat bladder 76b, and the pods 66 in thigh zone 60 collectively define a thigh zone bladder 78. It will be understood that bladders 74, 76a, 76b, and/or 78 can be implemented, in alternative embodiments, in manners other than pods, such as, but not limited to, elongated bladders, flat bladders, can-shaped bladders, or still other shapes.

Figure 4:
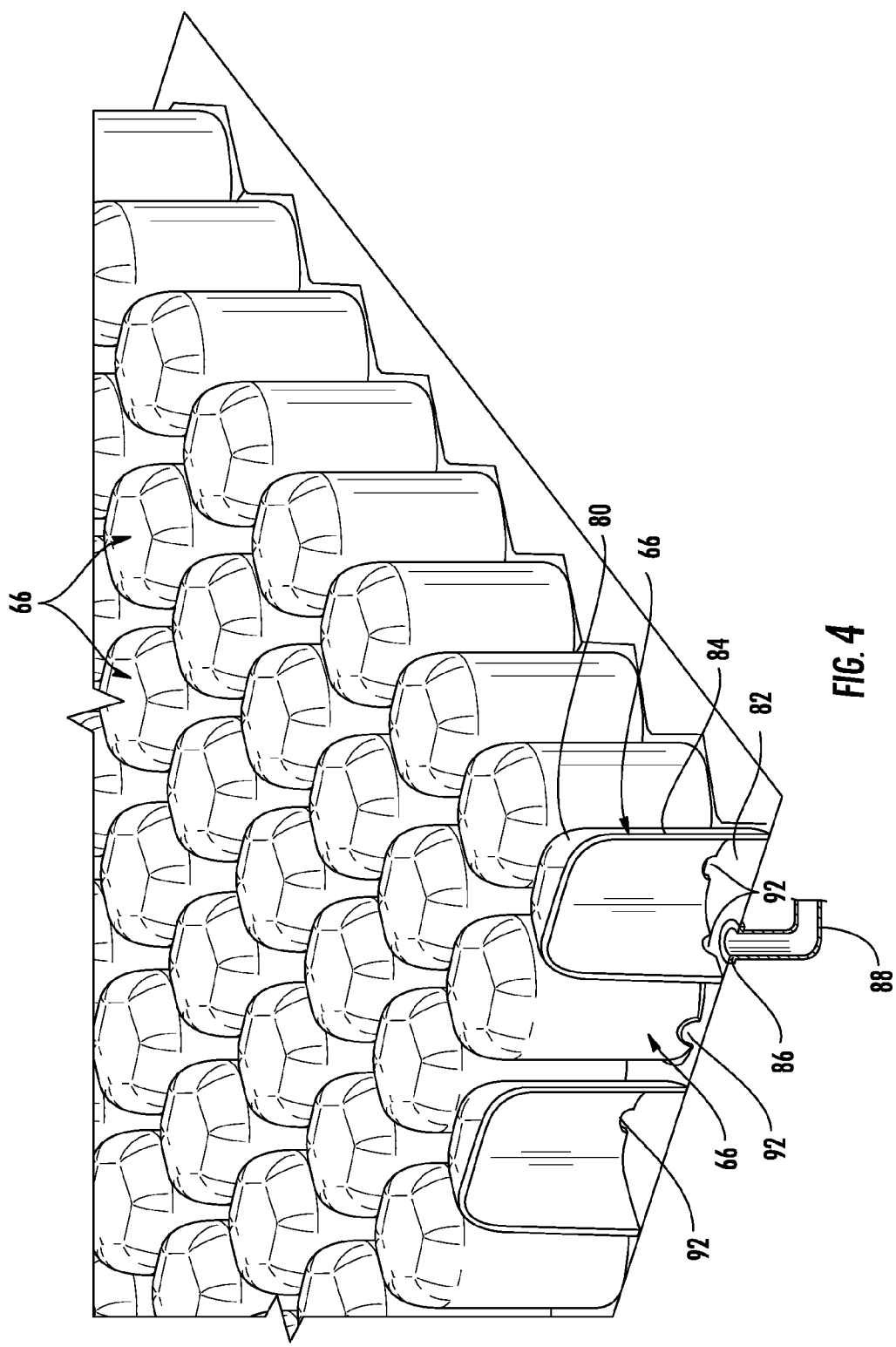
FIG. 4 is a partial perspective view of a plurality of bladders implemented as pods that are included in the patient support of FIG. 2.

FIG. 4 provides greater detail of one embodiment of pods 66. Each pod 66 includes a top surface 80, a base 82, and a sidewall 84. In at least one of the pods 66 in each bladder or each zone 54, an opening 86 is defined that is adapted to be coupled to an air hose 88. Air hose 88 extends to a pump box 90 (FIG. 5) which includes an air pump, blower, or other source of air that may be supplied to air hose 88 for delivery to the corresponding pods 66. As can be seen in FIG. 4, the pod 66 having opening 86 defined in its base 82 further includes a plurality of side openings 92 defined in side wall 84 generally near base 82. Side openings 92 provide fluid communication with adjacent pods 66. Thus, air delivered via hose 88 will be delivered not only to the pod 66 having opening 86 defined in its base 82, but it will also be delivered to all adjacent pods that are in fluid communication with side openings 92. Those adjacent pods may further include their own side openings 92, which will further distribute the supplied air to more pods. The inclusion of side openings 92 is arranged so that all of the pods 66 within a given zone 54 or a defined bladder are interconnected by one or more side openings 92. The pods at the edges of a zone 54 will not include side openings 92 in their exterior sides, thereby providing fluid isolation from neighboring zones. Consequently, all of the pods 66 within a given zone 54 will be in fluid communication with each other, and will generally have the same air pressure. In some embodiments, more than one air hose 88 may be connected to a given zone 54, and in some embodiments, separate air hoses 88 may be used for supplying air to the zone 54 and for removing air from the given zone 54. Regardless of the embodiment, control or pump box 90 oversees the delivery of air to, and/or the release of air from, the various zones 54.

Figure 5:
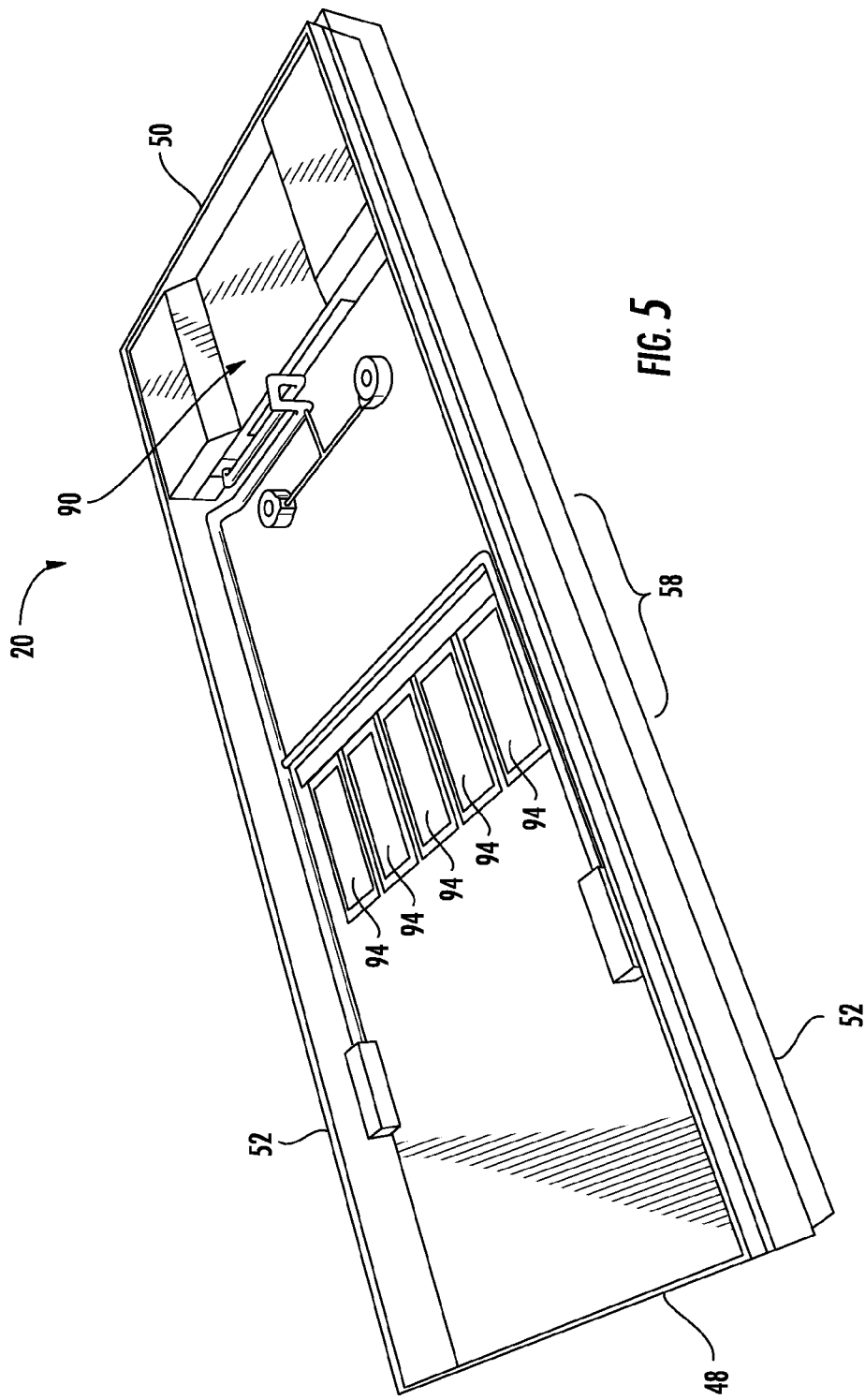
FIG. 5 is a perspective view of the patient support of FIG. 3 shown with the bladders, foam, and other cushioning removed to illustrate the layout of a plurality of depth sensors and a control box.

FIG. 5 shows patient support 20 with all of the pods 66 and most of the foam crib 70 removed therefrom. As can be seen, pump box 90 is positioned at foot end 50 of patient support 20 and, while not shown, includes one or more pumps or blowers for supplying air to the pods 66, a manifold having an assembly of controllable valves for controlling the air pressure inside of each zone 54, as well as—in some embodiments—one or more circuit boards for carrying out the control algorithms described herein. As can also be seen in FIG. 5, patient support 20 further includes a plurality of depth sensor plates 94 positioned generally laterally across seat zone 58 of patient support 20. Depth sensor plates 94 are used to measure how far a patient lying on the patient support 20 has sunk into seat bladders 76a and 76b. Depth sensor plates 94 make these measurements generally at the locations shown in FIG. 5. Thus, in the embodiment of FIG. 5, where there are six total depth plates 94, three depth sensor plates 94 will make three measurements of patient depth at three different, laterally spaced locations within right seat zone 58a, while the three other depth sensor plates 94 will make three measurements of patient depth at three different, laterally spaced locations within left seat zone 58b. Collectively, depth sensor plates 94 will make six depth measurements that span patient support 20 from one side 52 to the opposite side 52 across seat zone 58.

Figure 6:
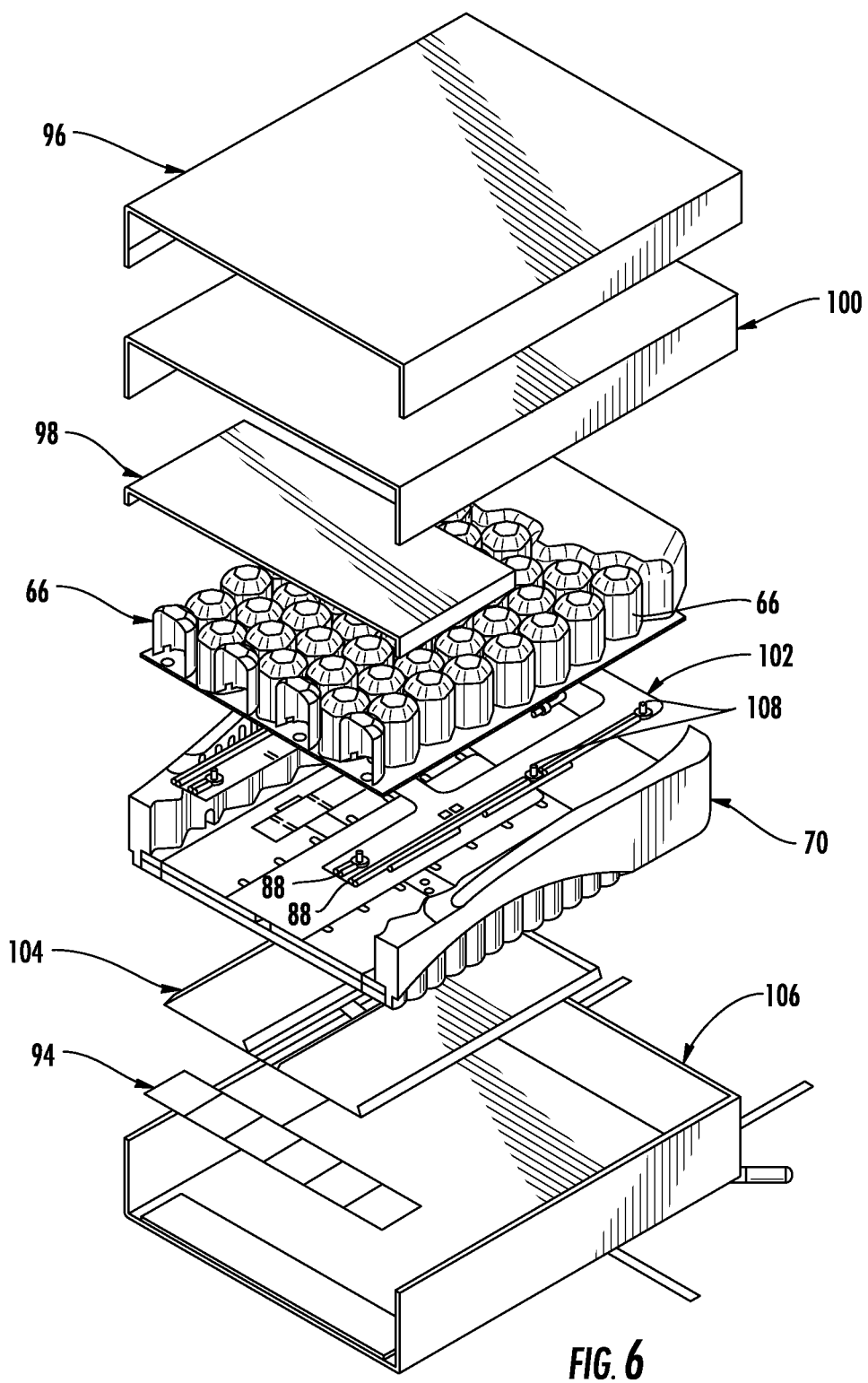
FIG. 6 is a partial, exploded view of the patient support of FIG. 2 showing its internal components in the support's seat and back zones.

As seen in FIG. 6, which illustrates various components of patient support 20 in back zone 56 and seat zone 58, patient support 20 includes a top cover 96, a fire barrier layer 100, a layer of conductive fabric 98, pods 66, a fabric manifold 102, foam crib 70, a plurality of turning bladders 104, six depth sensor plates 94, and a bottom cover 106. Top cover 96 may be made of any conventional material used in the manufacture of hospital mattresses, such as, but not limited to, a knit polyester, and/or a polyurethane.

Fire barrier 100 is positioned underneath top layer 96 and is made of any suitable material that resists the spread of fire. Such materials may vary. In one embodiment, fire barrier 100 may be made of, or include, Kevlar® (poly-paraphenylene terephthalamide), or other brands of para-aramid synthetic fibers. Other materials may alternatively be used.

Conductive fabric 98 functions to assist depth sensor plates 94 which, in the embodiment shown, are capacitive sensors whose output changes as a patient moves closer or farther away from them. More specifically, conductive fabric 98 functions in a manner similar to the top plate of a parallel plate capacitor, while depth sensor plates 94 form the bottom plates of the parallel plate capacitor. Thus, as the vertical distance between conductive fabric 98 and any of the depth sensor plates 94 changes, the capacitance between the fabric 98 and the plate(s) 94 will change. This change is detected by a detector circuit 112 (FIG. 7) that is electrically coupled between fabric 98 and each of the depth sensor plates 94. That is, one or more wires (not shown) are electrically coupled to fabric 98 and the detector circuits 112, while one or more other wires (not shown) are connected between each plate 94 and the detector circuit 112. Conductive fabric 98 may be any commercially available fabric that is electrically conductive, or it may be an electrically conductive foil, or any other material that is electrically conductive, and that is flexible enough to not significantly alter the flexibility of patient support 20 in that region.

Pods 66, as have been described herein, are inflated and deflated in groups (zones 56, 58a, 58b, and 60) under the control of pump box 90 and its associated control circuitry. The fluid connections between the pods 66 and pump box 90 are established by a plurality of hoses 88 that run between pump box 90 and various of the pods 66. Hoses 88 are housed within fabric manifold 102. Hoses 88 each include one or more connectors 108 for fluidly connecting the hose to one or more of the pods 66.

Turn bladders 104 are positioned underneath foam crib 70 and are used to help turn a patient positioned on top of patient support 20. To that end, turn bladders 104 extend generally longitudinally in a direction from head end 48 to foot end 50 and are each separately and independently inflatable and deflatable. The inflation of turn bladders 104 is controlled by pump box 90 and its associated circuitry.

Figure 7:
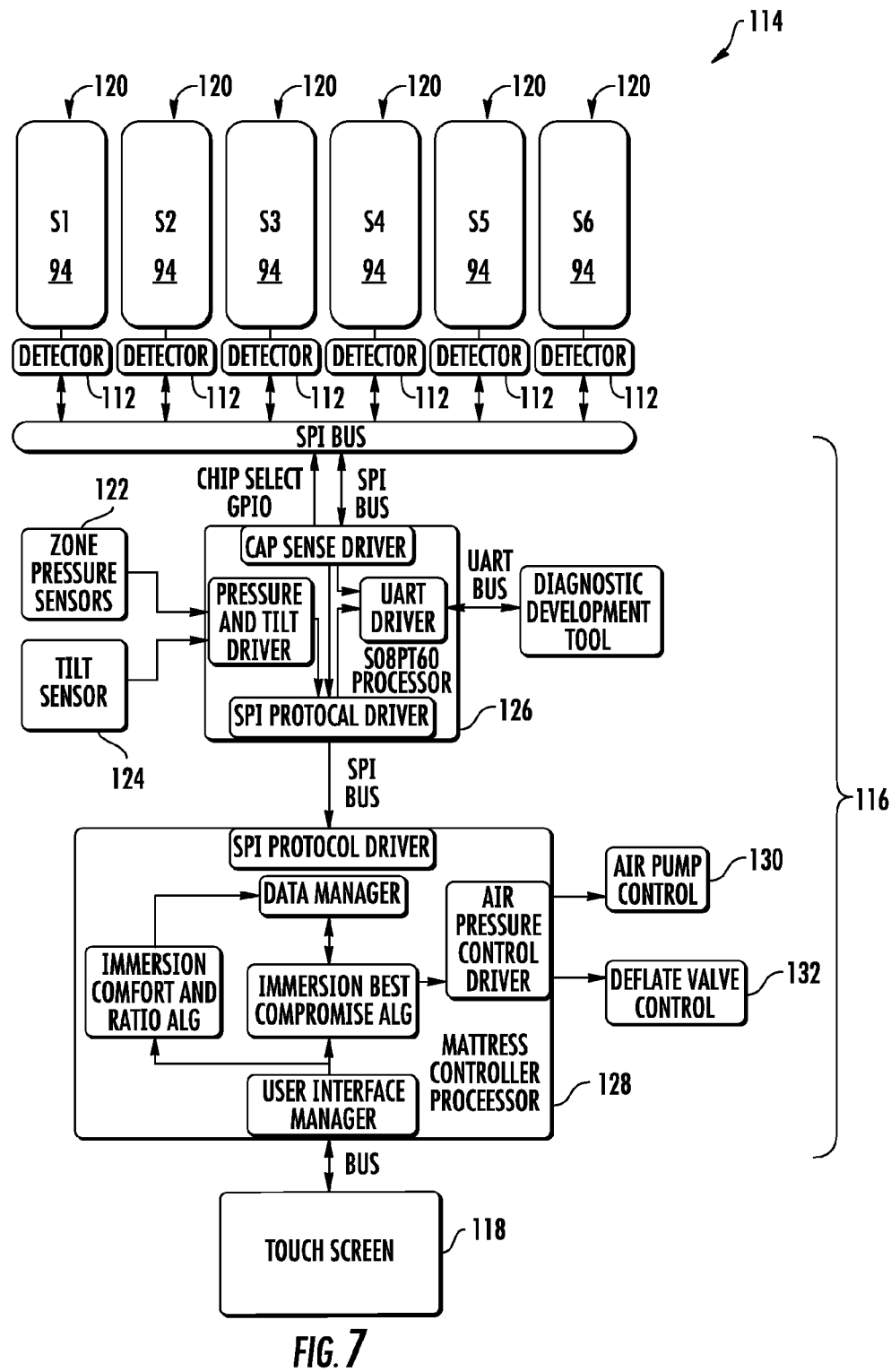
FIG. 7 is a schematic diagram of one embodiment of a control system that may be used in any of the patient supports described herein.

Each sensor plate 94 is a generally planar sheet of electrically conductive material, such as copper or other electrically conductive material. Each sensor plate 94 is electrically isolated from the other sensor plates 94. An insulation and shielding layer 110 is positioned underneath the sensor plates 94. Insulation and shielding layer 110, in one embodiment, includes upper and lower electrically insulating layers that surround six electrical shields. The electrical shields are electrically conductive and may be electrically coupled to the capacitive detector circuits 112 (FIG. 7). The electrical shields serve to limit capacitive interference that might otherwise result from the metal components of frame 30 of patient support apparatus 22.

FIG. 7 shows one embodiment of a control system 114 that may be implemented to control patient support 20 in the manners described herein. Other types, arrangements, and/or configurations of control systems may alternatively be used. Control system 114 includes a controller 116, a user interface 118, and a plurality of depth sensors 120. User interface 118 may be the same as user interface 38, discussed above, which is incorporated into footboard 36 of patient support apparatus 22, or it may be stand-alone user interface. Such stand-alone user interfaces may include user interfaces that are incorporated into pedestals that may be removable mounted on patient beds, such as patient support apparatus 22. In the embodiment shown in FIG. 7, user interface 118 is a touch screen. It will be understood that other types of user interfaces may be used, including buttons, switches, knobs, lights, and/or displays.

Each depth sensor 120 includes one of depth sensors plates 94, a corresponding detector 112, conductive fabric 98, and, in some embodiments, a shield (not shown) positioned underneath the sensor plate 94. Detector 112 may be any circuitry capable of detecting the varying capacitance between plate 94 and conductive fabric 98. In one embodiment, detector 112 includes an AD7747 capacitance-to-digital converter manufactured by Analog Devices of Norwood, Mass. Other types of detector circuitry may be used in other embodiments. Whatever the circuitry used, detectors 112 detect the capacitance levels between plates 94 and conductive fabric 98, which provide an indication of the vertical distance between plates 94 and fabric 98, which in turn indicates how deeply a patient is currently immersed in different areas of seat zone 58. In the embodiment illustrated, there are six separate detector circuits 112, thereby generating six separate measurements of patient depth in the seat zone 58. In one embodiment, depth sensors 120 each generate capacitive measurements multiple times a second, while in other embodiments, measurements are made at different frequencies.

Controller 116 is in electrical communication with both user interface 118 and depth sensors 120, as well as a plurality of air pressure sensors 122 and, in the illustrated embodiment, one or more tilt sensors 124. Air pressure sensors 122 measure the current air pressure inside each of the bladders of patient support 20 (e.g. back bladder 74, seat bladders 76a and 76b, thigh bladder 78, and pillow bladder 68). As was noted, each of these bladders generally corresponds to zones 56, 58a, 58b, 60, and 64, respectively. Tilt sensors 124 measure the angular orientation one or more portions of patient support 20, and/or they measure the entire angular orientation of patient support 20. In some embodiments, as was discussed previously, tilt sensors 124 are omitted and patient support 20 instead receives tilt data from one or more angle sensors that are incorporated into patient support apparatus 22. In still other embodiments, patient support 20 is implemented without any tilt sensors 124, and without receiving any tilt data from patient support apparatus 22.

Controller 116, in the embodiment shown in FIG. 7, includes two separate circuit boards: a sensor circuit board 126 and a main control circuit board 128. Sensor circuit board 126 receives the electrical signals from all of the various sensors and oversees the operation of these sensors (e.g. depth sensors 120, air pressure sensors 122, and tilt sensors 124). The data gathered from these various sensors is forwarded from sensor circuit board 126 to main control circuit board 128. In the embodiment shown, this data is forwarded via a serial peripheral interface (SPI) bus, although it will be understood that other buses may be used for this purpose. Main circuit board 128 is programmed, or otherwise configured, to carry out the control algorithms that will be described in more detail below. Generally speaking, main circuit board 128 determines the suitable inflation levels (e.g. a desired air pressure or—for those bladders with depth sensors 120—a desired patient depth) for all of the various bladders and controls necessary valves, air pump, and other aspects necessary to implement and maintain those suitable inflation levels. More specifically, main circuit board 128 is in communication with an air pump control 130 and a plurality of deflation valves 132. By way of suitable electrical signals sent to pump control 130 and valves 132, main control board 128 is able to implement and maintain the suitable inflation levels of the various bladders.

At shown in FIG. 7, each board 126 and 128 includes a processor, which may be a microprocessor or a microcontroller. Indeed, each circuit board 126 and 128 may include any electrical component, or group of electrical components, that are capable of carrying out the algorithms described herein. In many embodiments, circuit boards 126 and 128 will be microprocessor based, although not all such embodiments need include a microprocessor. In general, circuit boards 126 and 128 will include any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. It will further understood by those skilled in the art that controller 116 may be implemented in different forms from the two boards 126 and 128 illustrated in FIG. 7. Such variations may include combining the functions of both boards 126 and 128 onto a single board, or further distributing the functions of these boards onto more than the two boards 126 and 128 shown in FIG. 7.

Figure 8:
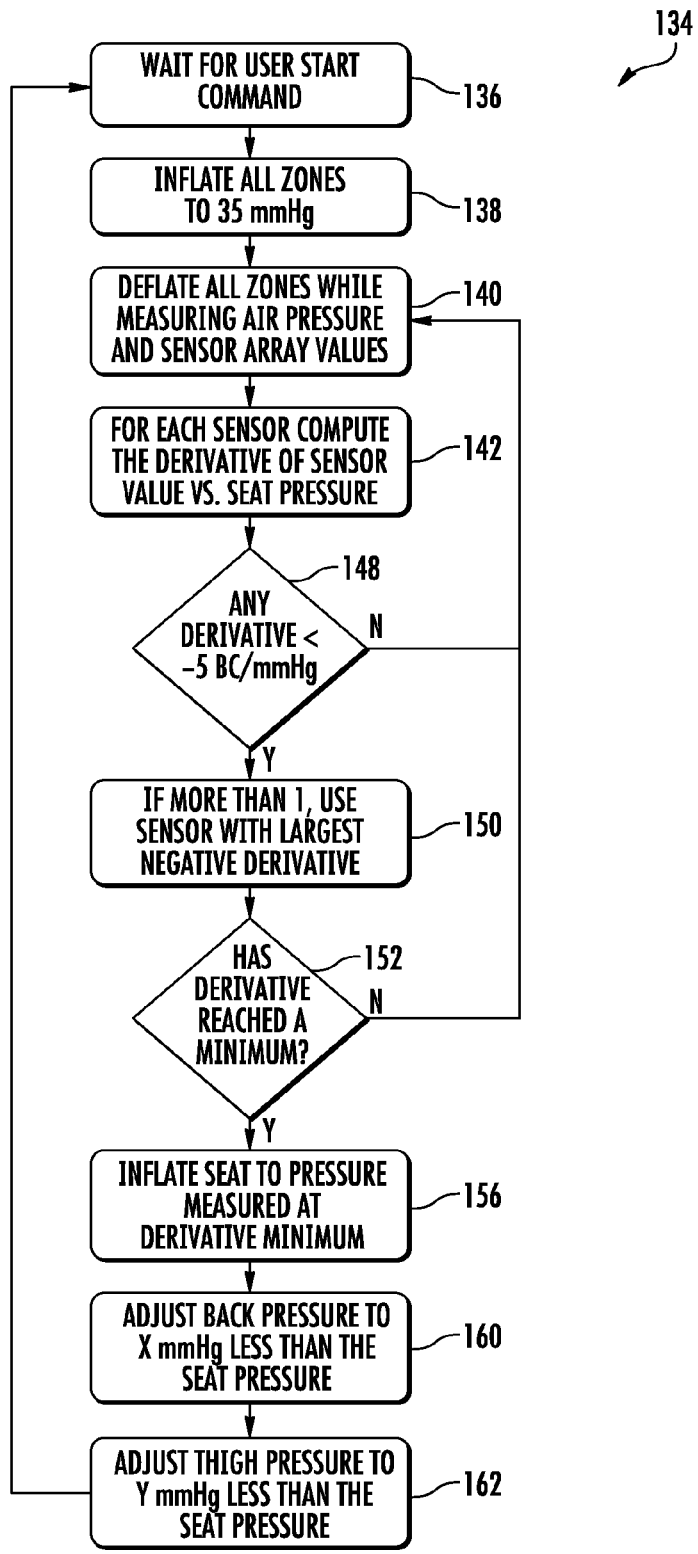
FIG. 8 is a flowchart illustrating an exemplary algorithm that may be used to determine a suitable inflation level for one or more bladders within any of the patient supports described herein.

FIG. 8 illustrates an inflation control algorithm 134 that, in one embodiment, is carried out by controller 116. Controller 116 may carry out this algorithm in different manners. In one manner, algorithm 134 is split amongst boards 126 and 128, while in another manner, all of the steps of algorithm 134 are carried out by main control board 128. Regardless of the specific manner of implementing control algorithm 134, inflation control algorithm 134 begins at an initial step 136 in which controller 116 waits for a user command to start the algorithm. The user command originates from user interface 118 after a user, such as a nurse or other caregiver, presses a button, touches a touch screen, or otherwise manipulates a control thereon that indicates he or she wishes to have patient support 20 automatically determine a suitable inflation level for the bladders of patient support 20. Initial step 136 may commence with a patient either on or off of patient support 20. If it commences with no patient supported on patient support 20, a patient must be positioned on patient support 20 prior to the commencement of step 140, discussed below.

After controller 116 receives a start command at initial step 136, it proceeds to an inflation step 138 where it begins inflating all of the bladders to a preset upper threshold. This is carried out by sending appropriate control signals to air pump control 130 and closing and/or opening the necessary valves so that air is delivered from pump box 90 to the bladders. While other variations may be made, controller 116 inflates all of the bladders of patient support 20 at step 138 with the sole exception of the turning bladders 104. More specifically, controller 116 inflates back bladder 74, seat bladders 76a, and 76b, and thigh zone bladder 78 to the preset upper threshold. In the embodiment shown in FIG. 8, the preset upper threshold is an air pressure equal to 35 millimeters of mercury (mmHg), although different thresholds can be used. In general, the upper threshold is set so that the patient sinks in very little, if at all, at the upper threshold inflation level. Controller 116 carries out this inflation in a closed loop manner, receiving feedback from pressure sensors 122. Each zone 54 includes at least one pressure sensor that repetitively indicates to controller 116 the current air pressure inside of that zone. Controller 116 is therefore able to monitor the pressure inside each of the zones 54 as they are being inflated toward the threshold pressure, and terminates the inflation for each zone 54 once it reaches the upper threshold pressure.

After the completion of step 138, controller 116 moves onto deflation step 140. As was noted above, deflation step 140 should not commence until a patient is positioned on patient support 20. In some embodiments, controller 116 is programmed to not even start inflation step 138 until a patient is positioned on the patient support. Controller 116 may determine patient presence and absence on patient support via communication with the load cells built into patient support apparatus 22 that can detect patient weight, or patient support 20 may determine patient presence by including its own sensors. In other embodiments, controller 116 starts control algorithm 134 regardless of whether a patient is present on patient support 20, and it is up to the caregiver to ensure a patient is positioned thereon prior to initiating the start command at step 136.

During deflation step 140, controller 116 begins deflating the air inside of right and left seat zones 58a and 58b. While deflating the right and left bladders 76a and 76b in these zones 58a and 58b, respectively, controller 116 continuously records measurements of depth from each of the six depth sensors 120 while also continuously recording measurements of air pressure inside of right and left seat bladders 76 and 76b. These measurements are recorded in a memory (not shown) accessible to controller 116, or on a memory within controller 116. These measurements are recorded in a manner that preserves the relationship between depth and pressure as the bladders is deflated. In other words, a measurement of depth and pressure are both made simultaneously, or nearly simultaneously, at a given time, and controller 116 records in memory that these two values correspond in time with each other. This enables controller 116 to know what the depth reading was for a given pressure, or vice versa.

Figure 9:
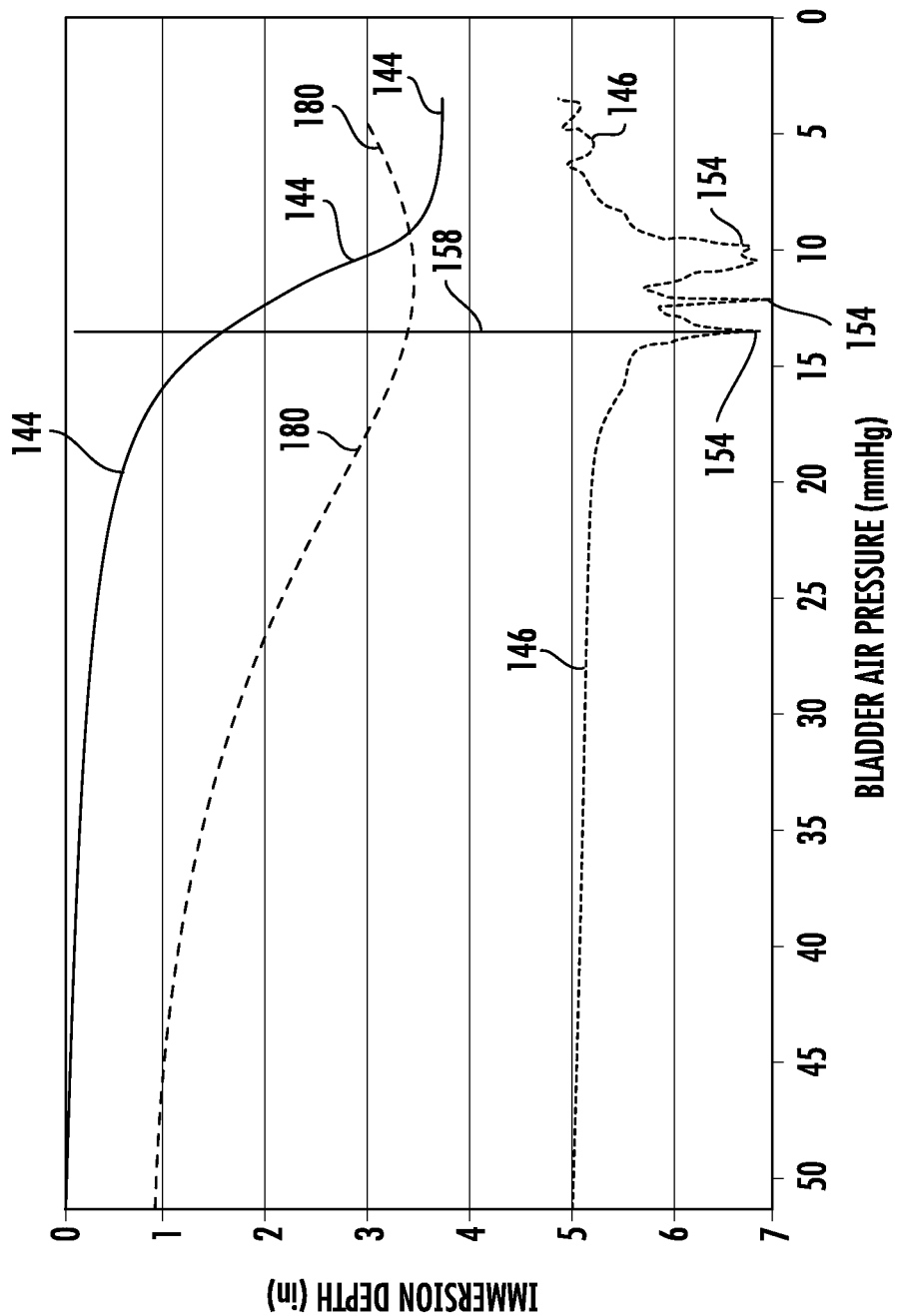
FIG. 9 is a plot of exemplary data showing a relationship between immersion depth and air bladder pressure when a patient is positioned on the patient support and the air pressure is changed.
Figure 10:
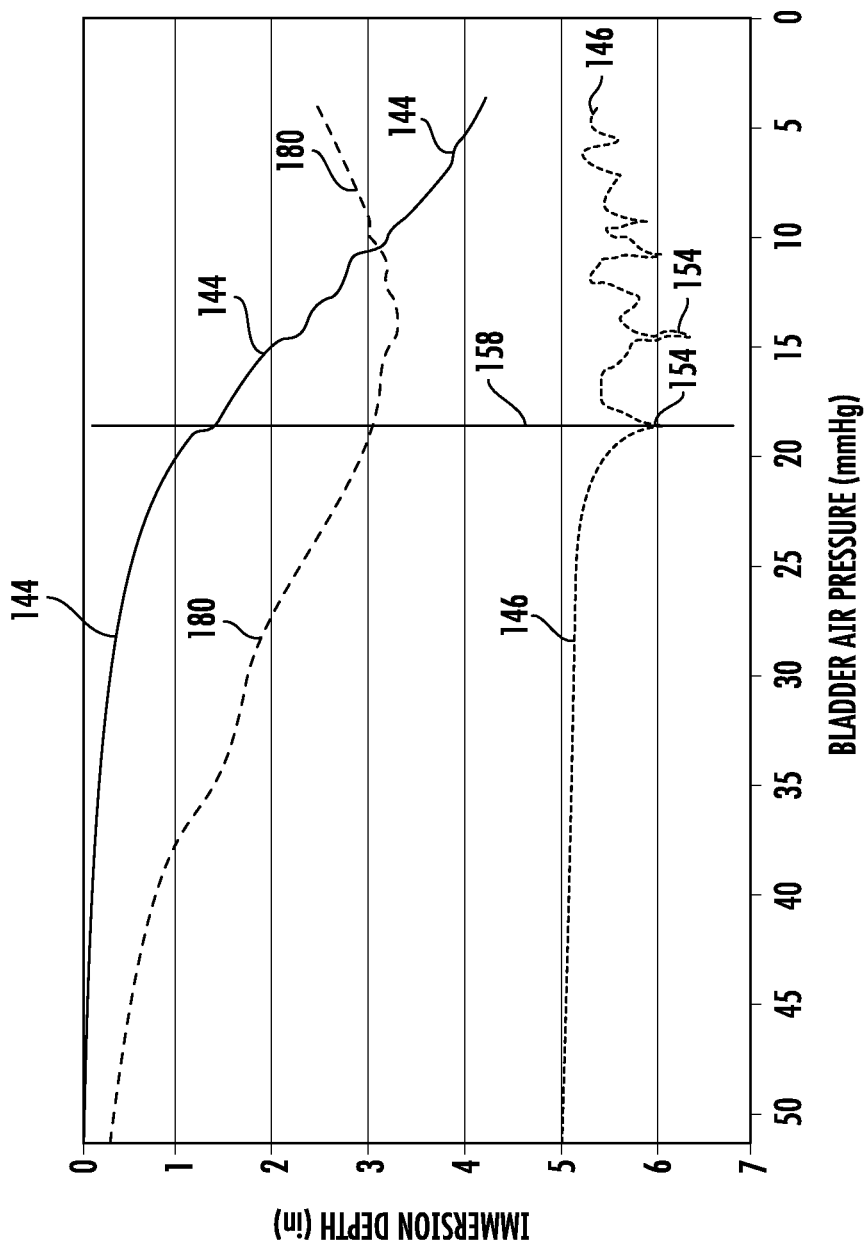
FIG. 10 is plot of different exemplary data showing a relationship between immersion depth and air bladder pressure when a patient is positioned on the patient support and the air pressure is changed.

FIGS. 9 and 10 show two examples that graphically plot the data which controller 116 is recording during step 140. While controller 116 does not actually plot this data, the plots of FIGS. 9 and 10 provide a useful way of illustrating the type of data that controller 116 is generating, and the subsequent analyses of this data that it performs. In both of these FIGS., the air pressure measurements are shown plotted on the x-axis, while the depth measurements from one of the depth sensors 120 are shown on the y-axis. Further, in both of these diagrams, the x-axis shows the air pressure in reverse order, that is, the air pressure decreases from left to right. This is done merely as one possible example. The x and y axes could be reversed, and the order of the pressure values could be change, if desired. For each depth sensor 120, controller 116 stores the depth sensor data that was gathered for that depth sensor 120 along with the corresponding air pressure data that was recorded simultaneously, or nearly simultaneously, with the depth sensors measurements. FIGS. 9 and 10 show a depth-versus-pressure plot 144 of this data. The data used to generate these plots 144 is merely exemplary of the types of data that may be gathered by controller 116 for a particular patient after controller 116 proceeds through steps 136-140 of algorithm 134.

Upon completing deflation step 140, controller 116 proceeds to a derivative calculation step 142. During derivative calculation step 142, controller 116 computes the mathematical derivative of the depth measurements with respect to the air pressure measurements for the entire set of depth and pressure measurements obtained during step 140. That is, controller 116 computes the rate of change of depth with respect to air pressure for each of the six depth sensors 120. For the three right-most depth sensors 120, the air pressure data will be the same because the three right-most depth sensors 120 are all positioned underneath right seat bladder 76a, which is a single bladder having a single air pressure. Similarly, for the three left-most depth sensors 120, the air pressure data will be the same for each other (but not necessarily the same as for the right-most depth sensors) because all three of these left-most sensors 120 are positioned underneath left seat bladder 76b, which is also a single bladder having a single air pressure. The depth measurements made by depth sensors 120, in contrast, may, and likely will, be different for each depth sensor because the patient's varying weight and morphology across the different portions of zones 58a and 58b or bladders 76a and 76b.

FIGS. 9 and 10 show graphically a derivative calculation plot 146 that corresponds to the depth-versus-pressure plots 144 in each of these FIGS. In other words, plot 146 in FIG. 9 is a plot of the derivative of curve 144 in FIG. 9, while plot 146 in FIG. 10 is a plot of the derivative of curve 144 in FIG. 10. The plots 144 and 146 need not actually be graphically displayed by control system 114, but controller 116 calculates the underlying data of each of these plots. The difference between the graphs in FIGS. 9 and 10 is presented here to merely show different examples of the types of data that control system 114 will generate during the performance of algorithm 134. In an actual system, data corresponding to six different graphs will be generated by controller 116—one for each of the six depth sensors 120. This data is then analyzed in accordance with algorithm 134 to determine a suitable inflation level (defined in terms of air pressure, patient depth, or some other control variable) for the various bladders of patient support 20.

After computing the derivatives of the depth-versus-pressure data for each of the depth sensors 120 at step 142, controller 116 moves to step 148 where it analyzes the calculated derivatives to see if any of the six sets of depth-versus-pressure data (one for each of the six depth sensors 120) have any derivative values that meet a threshold criteria. In the specific algorithm 134 shown in FIG. 8., the threshold is set at any derivatives which have a value less than five burst counts (BC) per millimeter of mercury (mmHG). The term "burst counts" refers to the outputs of the capacitive detector circuits 112 which, in the embodiment shown, measure capacitance using a charge count method. It will, of course, be understood by those skilled in the art that other methods of measuring capacitance may be used, including, but not limited to, oscillator-based approaches, bridge approaches, and still other approaches. It will further be understood by those skilled in the art that other methods of measuring patient depth may be used beside capacitive sensors, such at, but not limited to, inductive sensors, infrared light sensors, or other sensors. Regardless of the type of sensor, controller 116 analyzes the slope of the depth-versus-pressure data and looks for any slopes that exceed a threshold maximum value, or are less than a threshold minimum value, and that value may be defined in whatever terms are appropriate for that particular sensor. In the illustrated example, the slope is shown defined in terms of burst counts per millimeter of mercury. Other units may be used.

If controller 116 does not detect any slopes that meet the criteria defined in derivative analysis step 148, then controller 116 returns to step 140 where it continues deflating the bladders, gathering more data, and repeating steps 140, 142, and 144. This loop will continue until at least one derivative is found that matches the criteria of step 148. (It should be noted that the threshold criteria of step 148 is set so that, unless a patient is mistakenly absent from patient support 20 during algorithm 134, the criteria of step 148 will be fulfilled for at least one depth sensor 120 at some point during the deflation of patient support 20.) Once controller 116 determines that the derivative of the depth-versus-pressure data from at least one depth sensor 120 has at least one value that meets the threshold of step 148, controller 116 moves to selection step 150.

At selection step 150, controller 116 determines whether there is more than one depth sensor 120 that has a derivate plot 146 that, at some point in the plot, exceeds the threshold defined in step 148. If so, controller 116 selects which data from the multiple depth sensors 120 meeting the criteria of step 148 to use. In other words, selection step 150 involves selecting which of the six depth sensors 120 has generated data that controller 116 is going to use in determining the suitable inflation level of seat bladder 76. Controller 116 makes this selection by choosing which derivative plot 146 has the largest negative value. This means that controller 116 looks at the data from the sensors 120 and chooses the sensor 120 where the depth-versus-pressure plot 144 has the steepest downward slope.

An example of this choice can be seen graphically by examining FIGS. 9 and 10. Suppose, for purposes of illustration, that FIG. 9 graphically depicted the data generated by a first one of depth sensors 120, and that FIG. 10 graphically depicted the data generated by a second one of depth sensors 120. Further, suppose that both of the derivative plots of FIGS. 9 and 10 met the criteria of step 148 of algorithm 134 and that controller 116 was confronted with having to choose which set of data to use—that of FIG. 9 or that of FIG. 10. A visual comparison of FIGS. 9 and 10 reveals that the depth-versus-pressure plot 144 of FIG. 9 has a steeper downward slope than the plot 144 of FIG. 10. Accordingly, controller 116 will choose to use the data from the depth sensors 120 that corresponds to FIG. 9.

After selecting the depth sensor 120 to use at selection step 150, controller 116 moves to step 152, where it determines whether the derivative of the depth-versus-pressure plot 144 for the depth sensor 120 selected at step 150 has reached a local minimum 154 (FIGS. 9 and 10). If no local minimum in the derivative plot 146 has yet been reached, controller 116 returns to step 140 and repeats the steps previously described. At some point, after repeating any necessary steps, controller 116 will eventually determine at step 152 that a local minimum in the derivative curve 146 has been reached for one of the depth sensors 120. When that determination is made, controller 116 moves to a re-inflation step 156.

At re-inflation step 156, controller 116 starts inflating the bladders 76a and 76b of seat zones 58a and 58b until the air pressure inside of them reaches the air pressure corresponding to the air pressure at the local minimum 154 identified in step 152. In other words, when controller 116 eventually determines the first local minimum at step 152, controller 116 has successfully determined the desired inflation level of seat zone 58—it is either the air pressure corresponding to that local minimum, or it is the depth corresponding to that local minimum, which are alternative ways of achieving the same thing. In other words, controller 116 at step 156 will re-inflate the seat bladders until either the air pressure reaches the air pressure corresponding to local minimum 154, or until the currently measured depth reaches the depth corresponding to local minimum 154. The result should be the same in either case.

FIGS. 9 and/or 10 can be used to illustrate this more clearly. Suppose, for example, that the data of FIG. 9 was the data used by controller 116 in determining whether a local minimum 154 had been reached at step 152. While FIG. 9 shows multiple local minimums 154, this is for illustration purposes only. Because algorithm 134 generates data during the deflation of patient support 20 (as opposed to during the inflation of patient support 20), the left-most local minimum 154 shown in FIG. 9 will be the first (and likely only) local minimum detected by controller 116. The additional local minima 154 to the right of this might be detected, depending upon how close they are to the first local minimum, and/or depending upon how much additional data controller 116 is configured to gather. However, regardless of whether or not multiple local minima 154 are detected, controller 116 selects the first local minimum 154 and sets the suitable inflation level, graphically indicated by line 158 in FIG. 9, equal to either the air pressure measurement or depth measurement that correspond to it. In other words, suitable inflation level 158 in FIG. 9 identifies both an air pressure and a depth. The air pressure it defines is approximately 13 mmHG in this example. The depth it identifies is approximately 1.5 inches of immersion into patient support 20 (the depth at the intersection of plot 144 and line 158). At step 156, controller 116 re-inflates seat bladders 76a and 76b until either the air pressure inside of them equals 13 mmHg, or the depth sensor that generated the data of FIG. 9 detects a depth of approximately 1.5 inches. This is the suitable level of inflation for seat zones 58a and 58b.

At steps 160 and 162, controller 116 determines the suitable levels of inflation for back bladder 74 and thigh bladder 78, which correspond to back zone 56 and thigh zone 60, respectively. In the embodiment shown in FIG. 8, algorithm 134 sets both of these inflation levels equal to an air pressure that is a fixed offset from the air pressure inside of seat zone 58. More specifically, at step 160, controller 116 sets the air pressure inside of back bladder 74 to a value that is X mmHg less than the air pressure inside of seat bladders 76a and 76b. The specific value of X may vary. In one embodiment, X is set equal to 10 mmHg. In other embodiments, X may take on other values. Thus, continuing with the example of FIG. 9, if controller 116 has determined the local minimum 154 is at 13 mmHg, and therefore has set the air pressure inside of seat bladders 76 equal to 13 mmHg, controller 116 will set the pressure inside of back bladder 74 at step 160 equal to 13 minus X mmHg, or in this specific example, 3 mmHg (13−10=3).

After setting the air pressure inside of back bladder 74 at step 160, controller 116 proceeds to step 162 where it adjusts the air pressure inside of the thigh bladder 78. In the embodiment of algorithm 134 shown in FIG. 9, controller 116 sets the thigh zone air pressure to be a value that is Y mmHg greater than the air pressure inside of seat bladders 76a and 76b. As with the value of X, the value of Y may also vary. In one embodiment, Y is equal to 5 mmHg. In other embodiments, other values may be used. Continuing with the example of FIG. 9, controller 116 would set the air pressure inside of thigh bladder 78 equal to 18 mmHg, which is five mmHg (Y) greater than the air pressure inside of seat bladders 76a and 76b (13 mmHg).

In an alternative embodiment, algorithm 134 is modified so that one or both of steps 160 and 162 used fixed ratios, rather than offsets from the air pressure inside of seat bladders 76a and 76b. In other words, for example, controller 116 will set the air pressure inside of back bladder 74 equal to an air pressure that matches a preset ratio with respect to the air pressure inside of seat bladders 76a and 76b. For example, step 160 could be modified so that controller 116 sets the back bladder pressure to be equal to, say, 90% of the seat zone air pressure. Similarly, step 162 could be modified so that controller 116 set the thigh zone air pressure to be equal to 105%, or some other fixed ratio value, of the air pressure inside of seat bladders 76a and 76b. Still further, in some embodiments, algorithm 134 is modified so that one of the thigh and back bladders is set as an offset from the seat zone air pressure, while the other of the thigh and back bladders has their air pressure set as a percentage of the seat zone air pressure.

It will further be understood that patient support 20 can be modified to include one or more depth sensors 120 in either or both of back zone 56 and thigh zone 60, in which case steps 160 and/or 162 of algorithm 134 would be modified so that the air pressure inside of the bladders corresponding to these zones was set in the same manner as the air pressure inside of seat zone 58 was set in steps 136 through 156 of algorithm 134. Still further, patient support 20 could be modified to include one or more bladders in foot zone 62, and the air pressure inside of those bladders could be set by using one or more depth sensors positioned therein, or by setting the air pressure as an offset to, or ratio of, the air pressure inside of another bladder.

After controller 116 completes step 162, it has completed algorithm 134. Algorithm 134 will then terminate and controller 116 will maintain the pressures inside of the seat, back, and thigh zone bladders at those determined in steps 156, 160, and 162, respectively. Pressure inside of head or pillow bladder 68 may be set the same as that in back bladder 74, or it may be set differently.

In the embodiment shown, algorithm 134 is triggered based upon a user start command. In an alternative embodiment, step 136 of algorithm 134 is modified so that algorithm 134 will commence upon the occurrence of one or more triggering events. In one embodiment, the triggering events that will cause algorithm 134 to start include all of the following: a user initiates a start command via user interface 118; control system 114 determines that a patient has entered patient support 20 or patient support apparatus 22; control system 114 determines that a patient has changed positions on patient support 20 (e.g. turning, sitting up, rolling to one side or the other, etc.); control system 114 determines that an angular orientation of one of deck sections 40, 42, 44, or 46 has changed; control system 114 determines that the orientation of frame or litter 30 has changed (such as by adjusting elevation adjustment mechanisms 28 different amounts); and control system 114 detects that another object or another patient has entered or exited patient support 20. In yet other alternative embodiments, step 136 of algorithm 134 can be modified so that algorithm 134 will commence upon any subset of these triggering events, or any combination of one or more of these triggering events and any one or more other triggering events not specifically identified in the foregoing list.

When algorithm 134 is modified to include additional triggering events beyond a user manually initiating a start command, control system 114 can be configured to detect these additional triggering events in multiple different manners. Thus, for example, control system 114 can determine that a patient has entered patient support 20 by communications it receives from a control system onboard patient support apparatus 22 that includes load cells positioned to detect a patient's weight (and also, by implication, the absence or presence of a patient). The information from the load cells can also be used to detect when another patient or object enters or exits patient support 20 due to a significant weight change detected by the load cells. Similarly, patient movement on patient support 20 can be detected by the load cells of patient support apparatus 22 because such movement will result in changes in the patient's center of gravity, which can be detected by the load cells in the manner disclosed in the aforementioned and commonly assigned U.S. Pat. No. 5,276,432 issued to Travis. Angular changes due to the movement of any of deck sections 40, 42, 44, and 46 can be communicated to control system 114 from a controller on board patient support apparatus 22 that is in communication with angle sensors that measure the angles of these various deck sections. Similar angle sensors on patient support apparatus 22 can be used to detect, and report to control system 114, the angular orientation of frame 30. Alternatively, one or more angular sensors can be incorporated into patient support 20 so that changes in can be detected directly by control system 114, rather than relying on communication from components external to patient support 20.

Regardless of the specific number and kind of triggering events that cause controller 116 to re-start algorithm 134, the automatically-triggered operation of algorithm 134 helps ensure that a patient is supported on patient support 20 at suitable inflation levels, regardless of changes that are made which affect those inflation levels, and regardless of whether or not a caregiver is present. Thus, patient support 20 is, in at least one embodiment, configured to automatically, and repetitively, determine a suitable inflation level for the particular patient positioned thereon, and to update that inflation level appropriately based upon changes that affect the suitability of the inflation level. Further, because the suitable or desired inflation level is automatically chosen in a manner that reduces interface pressure (as will be discussed more below), patient support 20 will automatically adjust its inflation levels so that the likelihood of a patient developing pressure sores is reduced, regardless of caregiver presence, and regardless of changes that might otherwise lead to increases in interface pressure. In other words, patient support 20 will automatically adjust its inflation level based on triggering events so that the inflation level will be set at a level that generally minimizes, or comes close to minimizing, the interface pressure the patient is experiencing, thereby reducing the likelihood of pressure sores developing. Further, this will be done without requiring that a weight measurement of the patient first be taken, or any estimates of the patient size, morphology, or other patient aspects be made by a caregiver.

In yet another alternative embodiment, algorithm 134 can be modified so that, instead of gathering data while deflating seat bladders 76a and 76b, data was gathered while inflating these seat bladders. That is, algorithm 134 would start out by deflating—if not already deflated—the seat zone bladders until a preset minimum pressure was set. Thereafter, controller 116 would begin inflating the seat zone bladders while taking repetitive measurements of air pressure and depth for each of the six depth sensors 120. This would result in generating the data of FIGS. 9 and 10, for example, in a manner from right to left, rather than the left to right manner of the unmodified algorithm 134. It is expected that the result of this data gathering would be the same. Controller 116 would then choose the local minimum 154 that was detected last, instead of first, as the point defining the desired inflation level. Algorithm 134 would stop gathering data once a threshold maximum air pressure was reached, such as the 35 mmHg defined in step 138.

In yet another embodiment of algorithm 134, the suitable or desired level of inflation inside of seat bladders 76a and 76b is set independently. That is, instead of using data from one of the six depth sensors 120 to use for determining the inflation level of both bladders 76a and 76b, algorithm 134 can be modified so that data from one of the three depth sensors 120 under right seat bladder 76a is selected for determining the suitable inflation level of right seat bladder 76a, while data from one of the other three depth sensors 120 under left seat bladder 76b is selected for determining the suitable inflation level of left seat bladder 76b. The air pressure inside of the back and thigh zones can then be set to be either an offset to, or percentage of, a selected one of seat bladders 76a and 76b. Still further, patient support 20 can be modified to include a greater or smaller number of seat zone bladders 76, in which case algorithm 134 can be correspondingly modified.

It will further be understood by those skilled in the art that patient support 20 can be modified to include a greater, or lesser, number of depth sensors 120 than the six shown in the accompanying drawings. In one embodiment, only a single depth sensor is used, in which case algorithm 134 is modified to omit selection step 150, which is no longer necessary. Still further, the placement of the depth sensors 120 can be modified, such as, but not limited to, positioning one or more of the depth sensors 120 underneath one or more of the other bladders in patient support 20.

Figure 11:
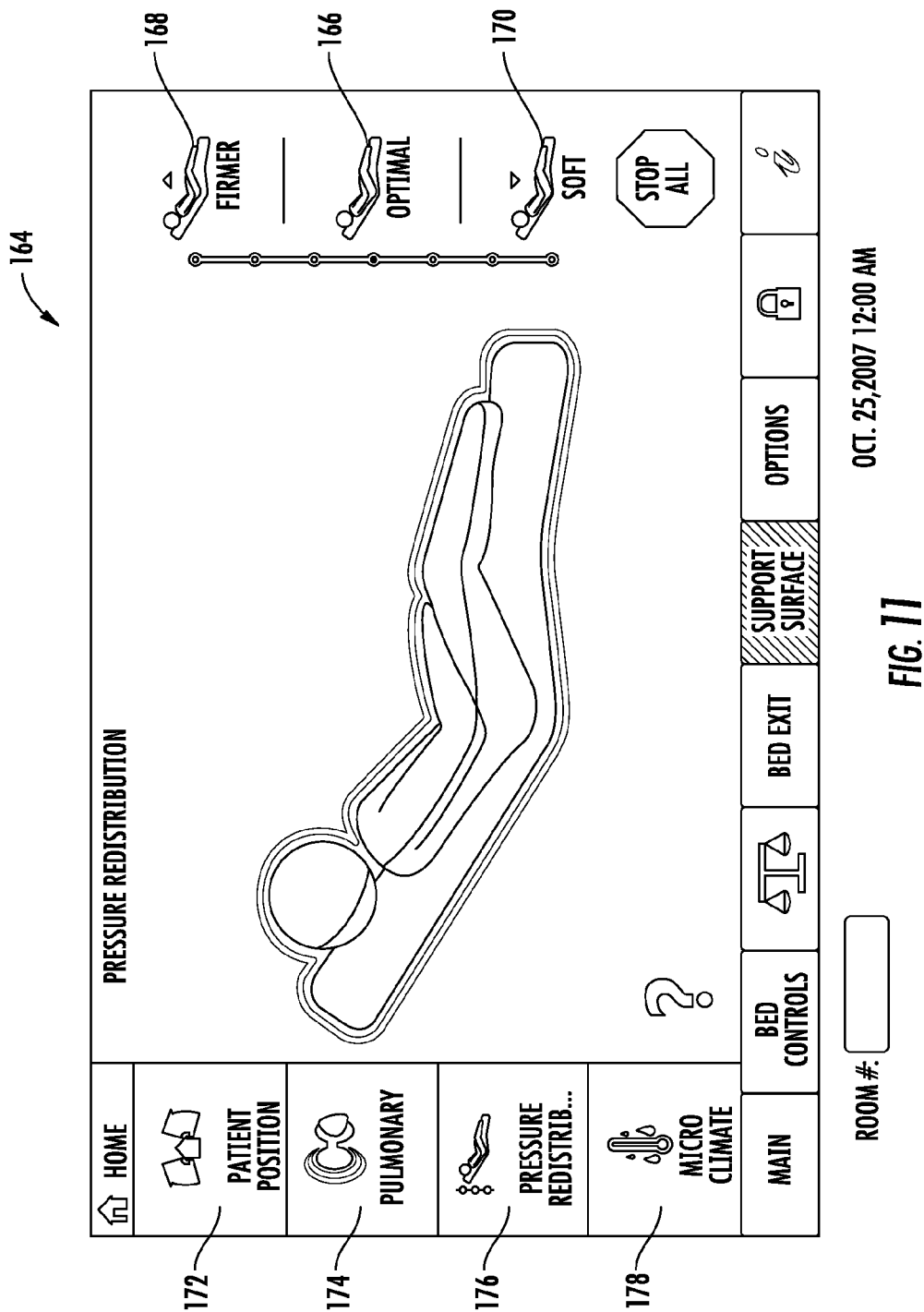
FIG. 11 is an illustrative screenshot that appears on a display and that may be used to control any of the patient supports described herein.

FIG. 11 illustrates one example of an image 164 that may be displayed on a touch screen, or other display screen, of user interface 118. Image 164 includes an "optimal" icon 166, a "firmer" icon 168, and a "softer" icon 170. Pressing on icon 166 will trigger controller 116 to run through algorithm 134, which will result in setting the inflation levels inside of patient support 20 at a level that is designed to minimize, or nearly minimize, the patient interface pressures experienced by the patient. If it is desired to alter those automatically determined inflation levels, a caregiver can press either of icons 168 or 170. Pressing icon 168 will cause controller 116 to increase the air pressure inside of all of the bladders 74, 76a, 76b, and, 78 an incremental amount. Pressing it N times will cause controller 116 to increase the air pressure N times the incremental amount, up to a safety limit, beyond which further inflation will not take place. Conversely, pressing icon 170 will cause controller 116 to decrease the air pressure inside of all of the bladders 74, 76a, 76b, and 78 an incremental amount, and pressing it N time will cause controller 116 to decrease the air pressure N times the incremental amount.

Image 164 of FIG. 11 also includes a patient positioning icon 172, a pulmonary icon 174, a pressure redistribution icon 176, and a microclimate icon 178. Image 164 will change depending upon which of these four icons a user presses (or otherwise selects). The image 164 shown in FIG. 11 is the image that corresponds to pressure distribution icon 176 being selected. If a user selects patient position icon 172, a different image will appear on the touch screen that include icons for controlling turning bladders 104. Pressing those icons will cause controller 116 to control the inflation and deflation of turning bladders 104 in the desired manner. If a user selects pulmonary icon 174, a different image will appear on the touch screen that includes icons for controlling pulmonary therapies that patient support 20 is capable of carrying out, such as percussion, or other therapies. Pressing one of these icons will thereby cause controller 116 to institute the inflation and deflation of the appropriate bladders necessary to carry out these therapies. Finally, if a user selects microclimate icon 178, this will cause yet a different image to appear on the touch screen that includes icons for controlling the microclimate aspects of patient support 20. Specifically, in one embodiment, patient support 20 is a low air loss mattress in which air can be made to continuously flow upward from patient support 20 to cool and/or dry the microclimate at the interface of the patient and patient support 20.

In addition to illustrating a graphical representation of the pressure and depth data that is generated by algorithm 134, FIGS. 9 and 10 also show patient interface pressure, which is not measured by patient support 20, but has been included on FIGS. 9 and 10 for purposes of demonstrating the usefulness of algorithm 134. Specifically, each of FIGS. 9 and 10 include a patient interface pressure plot 180 that shows the interface pressure that a patient experiences at the corresponding air pressures. The scale for the units of the patient interface pressure is not shown in FIGS. 9 and 10, but the absolute value of the interface pressure is not as important as illustrating that the desired inflation level 158 is at, or very near, the minimum in the patient interface pressure 180. This is true for the plots shown in both FIGS. 9 and 10. Thus, it can be seen that algorithm 134 automatically determines an inflation level that minimizes, or nearly minimizes, the patient interface pressure, which is important for reducing the likelihood of bed sores.

In addition to the modifications already discussed above, algorithm 134 may be further modified in still additional manners. In one embodiment, instead of searching for the first local minimum (left-most in FIGS. 9 and 10) in the derivative curve 146, controller 116 could be programmed to search for, and identify, the second local minimum 154. This second local minimum could then be used to define the suitable inflation level 158. Alternatively, controller 116 could be programmed to pick an air pressure that was somewhere between the first and second local minima 154. Still further, algorithm 134 could be modified to select an air pressure or depth that was a fixed offset from either the first or second local minima 154.

Stepping back from the details of algorithm 134, it can be observed that algorithm 134 monitors how much a patient sinks in relation to how much air is let out of the underlying seat bladders 76a and 76b. That is, after inflating bladders to the pressure of step 138, for each incremental release of air from bladders 76a, 76b, controller 116 monitors how much farther the patient sinks into bladders 76a, 76b. At first, the release of air causes very little change in pressure. This is seen in FIGS. 9 and 10, which show a generally straight and only slightly negatively sloped line 144 in the region from 50 mmHg down to roughly 20 to 25 mmHg. At about this region of the curve, further decreases in the air pressure (caused by releasing more air from bladders 76a, 76b) lead to a more precipitous increase in the immersion depth of the patient. It is believed that this is due to the fact that, in the region of the more steeply sloped section of curves 144, decrease in air volume (and air pressure) result predominantly in a person sinking into the mattress more, with little additional new surface area added between the top of patient support 20 and the patient himself. In other words, in the generally flat region of curves 144 (e.g. approximately 25 to 50 mmHg), it is believed that the predominant reaction of the system (patient and patient support 20) to further decreases in air pressure is to bring more and more of the surface area of the patient's body into contact with the top of patient support 20, while in the in the more steeply sloped section of curves 144, the more predominant reaction of the system is for the patient to sink in further, without much accompanying increase in the surface area of the patient's body that comes into contact with the top of patient support 20. Because increasing the surface area of the patient's body that comes into contact with patient support 20 is generally desired—because the greater surface area better distributes the patient's weight, thus decreasing patient interface pressure—further decreases in the air pressure in the generally flat regions of curves 144 lead more predominantly to distributing the patient's weight (as opposed to sinking into the surface). In contrast, in the more curved region of curves 144, further decrease in air pressure lead to greater changes in depth, as opposed to greater changes in surface area. Thus, decreasing the air pressure much past the beginning of the generally curved regions of curves 144 does little more to alleviate patient interface pressure. Consequently, selecting an air pressure in the region of curves 144 where the steeper slope starts leads to an air pressure that minimizes, or nearly minimizes, the patient interface pressure, which is why suitable inflation lines 158 are positioned in this region.

Controller 116 is thereby able to determine a optimized, or nearly optimized, level of inflation for seat bladders 76a, 76b, that reduces patient interface pressures to nearly as small as possible, while also preventing, to the extent possible, the over-immersion of a patient in patient support 20, which can lead to feelings of discomfort to the patient. Controller 116 is able to do this without resort to any look-up tables that store desired pressure values, or desired depths, for various types of patients, based on their weight, height, morphology, or other characteristics. Instead, controller 116 is able to uniquely tailor the inflation level of the bladders in patient support so as to provide an optimized level of interface pressure reduction and patient comfort to each individual that rests on patient support 20. Further, as was noted, this optimized level of inflation is, in at least one embodiment, automatically adjusted any time a triggering event occurs that may lead to the currently set level of inflation no longer being the optimized level. Some of such triggering events were discussed previously.

It will be understood that, while algorithm 134 was described above in terms of gathering air pressure and depth data, it could be modified to gather air bladder volume and depth data. That is, instead of making measurements of air pressure as air is allowed to escape during step 140, measurements could instead be made of the volume of air that is released from the bladder, and/or the volume of air remaining in the bladder. This volume data would be gathered in conjunction with the depth measurements. Controller 116 would then look for an inflection point in the graph of this data, just as it does in the graph of the air pressure versus depth data described above.

In another embodiment, controller 116 is configured to non-invasively monitor a patient's vital signs while the patient is positioned on patient support 20. This non-invasive monitoring of the patient's vital signs is carried out, in some embodiments, completely independently of the algorithms used to set the inflation level of the bladders. That is, regardless of how the inflation levels of the bladders are chosen and/or controlled, controller 116 is configured in some embodiments to determine either or both of a patient's heart rate and respiration rate.

When so configured, controller 116 determines a patient's heart rate and/or respiration rate by monitoring the outputs from both the pressure sensors 122 and the depth sensors 120. More specifically, in one embodiment, pressure and depth readings are monitored and compared to each other. When graphically represented, with the pressure readings on one axis and the depth readings on another axis, the data collected from these sensors will vary generally sinusoidally in response to the patient's breathing and respiration. These sinusoidal signals can be processed to determine both the patient's breathing rate and heart rate. Such processing can be accomplished by a variety of different means, such as, but not limited to, performing Fourier transforms on the data and identifying peak frequencies corresponding to those within the expected range of heart rates and the expected range of respiration rates.

A more detailed description of suitable processing of the depth and pressure measurements to determine heart rate and respiration rate is found in commonly assigned U.S. Pat. No. 7,699,784 issued Apr. 20, 2010 to applicants Wan Fong et al. and entitled SYSTEM FOR DETECTING AND MONITORING VITAL SIGNS, the complete disclosure of which is hereby incorporated herein by reference. Although this '784 patent describes a system for determining a patient's heart rate and breathing rate by analyzing signals generated from force sensors positioned under the patient, the same analysis can be applied to the pressure and depth signals generated from sensors 122 and 120 to yield heart rate and breathing rate.

The above description is that of several embodiments of the invention. Various alterations and changes can be made from these embodiments without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A patient support comprising:
an inflatable bladder;
a depth sensor adapted to generate a depth signal indicative of how deeply a patient positioned on said patient support sinks into said inflatable bladder;
an air pressure sensor adapted to generate an air pressure signal indicative of a level of air pressure inside of said inflatable bladder; and
a controller adapted to determine a suitable inflation level of said bladder by monitoring a rate of change of the depth signal with respect to the air pressure signal as the air pressure inside the bladder is changed.

2. The support of claim 1 wherein said controller determines the suitable inflation level after detecting an inflection point in a plot of the depth signal versus the air pressure signal.

3. The support of claim 1 wherein the controller monitors the rate of change of the depth signal with respect to the air pressure signal as the air pressure is lowered inside the bladder.

4. The support of claim 1 wherein the controller monitors the rate of change of the depth signal with respect to the air pressure signal as the air pressure is raised inside the bladder.

5. The support of claim 1 wherein said controller sets the suitable inflation level equal to an air pressure at which a derivative of the depth signal with respect to the air pressure signal is substantially equal to a local minimum.

6. The support of claim 1 wherein said inflatable bladder is incorporated into a mattress and positioned at a location adapted to support a patient's sacral area.

7. The support of claim 1 wherein said patient support includes:
a plurality of inflatable bladders;
a plurality of depth sensors, each depth sensor positioned inside a corresponding one of said plurality of inflatable bladders, and each depth sensor adapted to generate a depth signal indicative of how deeply a patient positioned on the patient support sinks into the corresponding inflatable bladder;
a plurality of air pressure sensors, each air pressure sensor adapted to generate an air pressure signal indicative of a level of air pressure inside of a corresponding one of said inflatable bladders; and
wherein said controller is adapted to determine the suitable inflation level based on all of the depth signals and all of the air pressure signals.

8. The support of claim 1 wherein said patient support further includes a bed frame having a support surface on which said bladder may be supported, said bed frame including a control panel adapted to control inflation of said bladder, said control panel including a control for causing said controller to re-determine said suitable inflation level.

9. The support of claim 1 wherein said bladder is incorporated into a mattress positionable on a bed frame, and said controller automatically re-determines the suitable inflation level if more than a threshold amount of patient movement is detected, or if an angular orientation of a portion of the bed frame changes by more than a threshold angular amount.

10. The support of claim 1 wherein said depth sensor includes a capacitive plate positioned generally horizontally underneath said bladder, and a flexible, electrically conductive sheet positioned above said bladder.

11. A patient support comprising:
a first inflatable bladder;
a second inflatable bladder;
a depth sensor adapted to generate a depth signal indicative of how deeply a patient positioned on said patient support sinks into said first inflatable bladder;
an air pressure sensor adapted to generate an air pressure signal indicative of a level of air pressure inside of said first inflatable bladder; and
a controller adapted to determine a suitable inflation level of said first inflatable bladder based upon readings from said depth sensor, said controller further adapted to control an air pressure inside of said second bladder so as to be equal to a fixed ratio with respect to, or to have a non-zero fixed offset from, the air pressure inside of said first inflatable bladder, said fixed ratio having a value other than one.

12. A patient support comprising:
an inflatable bladder;
a first depth sensor adapted to generate a first depth signal indicative of how deeply a patient positioned on said patient support sinks into a first portion of said inflatable bladder;
a second depth sensor adapted to generate a second depth signal indicative of how deeply a patient positioned on said patient support sinks into a second portion of said inflatable bladder;
an air pressure sensor adapted to generate an air pressure signal indicative of a level of air pressure inside of said inflatable bladder; and
a controller adapted to determine a suitable inflation level of said bladder by monitoring a rate of change of the first depth signal with respect to the air pressure signal and by monitoring a rate of change of the second depth signal with respect to the air pressure signal.

13. The support of claim 12 wherein said controller sets the suitable inflation level equal to an air pressure at which a derivative of either the first depth signal with respect to the air pressure signal or the second depth signal with respect to the air pressure signal is substantially equal to a local minimum.

14. The support of claim 12 wherein said inflatable bladder is incorporated into a mattress and positioned at a location adapted to support a patient's sacral area, and said inflatable bladder includes a plurality of pods.

15. The support of claim 12 wherein said first depth sensor includes: (1) a first capacitive plate positioned generally horizontally underneath said first portion of said bladder, and (2) a flexible, electrically conductive sheet positioned above said bladder; and said second depth sensor includes: (1) a second capacitive plate positioned generally horizontally underneath said second portion of said bladder, and (2) said flexible, electrically conductive sheet.

16. The support of claim 12 wherein said controller re-determines the suitable inflation level by inflating the bladder to a desired pressure, allowing air to escape from said bladder, and monitoring the rate of change of the first and second depth signals with respect to the air pressure signal as the air pressure inside the bladder is decreased.

17. A patient support comprising:
a first section having a first inflatable bladder,
a second section having a second inflatable bladder, said second section being positioned in an area adapted to support a sacral region of a patient when the patient lies on the patient support;

a depth sensor adapted to generate depth signals indicative of how deeply a patient positioned on said patient support sinks into said second inflatable bladder;

an air pressure sensor adapted to generate air pressure signals indicative of a level of air pressure inside of said second inflatable bladder; and a controller adapted to determine a suitable inflation level of said second bladder based upon said depth signals and said air pressure signals, and to determine a suitable inflation level of said first bladder based upon the suitable inflation level of said second bladder.

18. The support of claim 17 wherein said suitable inflation level of said first bladder is a fixed ratio, or has a fixed offset, with respect to the suitable inflation level of said second bladder.

19. The support of claim 17 wherein said controller determines the suitable inflation level of said second bladder by monitoring a rate of change of the depth signals with respect to the air pressure signals as the air pressure inside the bladder is changed.

20. The support of claim 17 wherein said first and second bladders both include a plurality of pods.

21. The support of claim 17 further including a third section having a third inflatable bladder, said third section being positioned on a side of said second section opposite said first section; and wherein said controller is adapted to determine a suitable inflation level of said third bladder based upon the suitable inflation level of said second bladder.

22. The support of claim 21 wherein said suitable inflation level of said third bladder has another fixed ratio, or fixed offset, with respect to the suitable inflation level of said second bladder.

23. The support of claim 21 further including a plurality of depth sensors for generating a plurality of depth signals indicative of how deeply a patient positioned on said patient support sinks into a plurality of different portions of said second inflatable bladder, wherein said controller determines the suitable inflation level of said second bladder by monitoring all of said plurality of depth signals.

24. The support of claim 23 wherein said controller determines the suitable inflation level of said second bladder by monitoring the rate of change of the depth signals with respect to the air pressure signals for each of the plurality of depth sensors.

25. The support of claim 24 wherein said controller determines the suitable inflation level of said second bladder by determining which of said plurality of depth sensors has the highest rate of change of its depth signal with respect to the air pressure signal.

* * * * *